(12) United States Patent
Maiocchi et al.

(10) Patent No.: US 10,682,427 B2
(45) Date of Patent: Jun. 16, 2020

(54) INTRA-OPERATIVE IMAGING

(71) Applicant: BRACCO IMAGING S.P.A., Milan (IT)

(72) Inventors: Alessandro Maiocchi, Monza (IT); Chiara Brioschi, Varedo (IT); Fulvio Uggeri, Codogno (IT); Giovanni Valbusa, Stresa (IT)

(73) Assignee: BRACCO IMAGING S.P.A., Milan (IT)

( * ) Notice: Subject to any disclaimer, the term of this patent is extended or adjusted under 35 U.S.C. 154(b) by 211 days.

(21) Appl. No.: 15/535,937

(22) PCT Filed: Dec. 18, 2015

(86) PCT No.: PCT/EP2015/080545
§ 371 (c)(1),
(2) Date: Jun. 14, 2017

(87) PCT Pub. No.: WO2016/097317
PCT Pub. Date: Jun. 23, 2016

(65) Prior Publication Data
US 2017/0340755 A1 Nov. 30, 2017

(30) Foreign Application Priority Data
Dec. 19, 2014 (EP) ..................................... 14199240

(51) Int. Cl.
*A61K 49/00* (2006.01)
*A61B 5/00* (2006.01)
(Continued)

(52) U.S. Cl.
CPC ........ *A61K 49/0056* (2013.01); *A61B 5/0071* (2013.01); *A61B 5/0091* (2013.01);
(Continued)

(58) Field of Classification Search
CPC ....... A61B 5/0071; A61B 5/0091; A61B 5/08; A61B 5/4041; A61B 5/4064;
(Continued)

(56) References Cited

U.S. PATENT DOCUMENTS

2014/0088384 A1 3/2014 Basilion

FOREIGN PATENT DOCUMENTS

| WO | WO2006-095234 A2 | 9/2006 |
| WO | 2008139206 A2 | 11/2008 |

(Continued)

OTHER PUBLICATIONS

Lanzardo, Stefania, et al. "A new optical imaging probe targeting alpha-v-beta-3 integrin in glioblastoma xenografts." Nov. 29, 2011. Contrast Media and Molecular Imaging. vol. 6. 449-458. (Year: 2011).*

(Continued)

*Primary Examiner* — Michael W Kahelin
(74) *Attorney, Agent, or Firm* — Vivicar Law, PLLC

(57) ABSTRACT

The present invention relates to the use of a NIR fluorescent probe comprising an aza-bicycloalkane based cyclic peptide labelled with a Cy5.5 dye moiety in the fluorescence-guided surgery of pathologic regions and to an optical imaging method that comprises using this fluorescent probe for the identification and demarcation of tumor margins during the surgical resection.

21 Claims, 5 Drawing Sheets

(51) Int. Cl.
*A61B 5/08* (2006.01)
*A61B 10/00* (2006.01)

(52) U.S. Cl.
CPC .............. *A61B 5/08* (2013.01); *A61B 5/4041* (2013.01); *A61B 5/4064* (2013.01); *A61B 5/4244* (2013.01); *A61B 5/4255* (2013.01); *A61B 5/4325* (2013.01); *A61B 5/4381* (2013.01); *A61B 5/444* (2013.01); *A61B 10/0041* (2013.01); *A61K 49/0032* (2013.01); *A61B 2505/05* (2013.01)

(58) Field of Classification Search
CPC ... A61B 5/4244; A61B 5/4255; A61B 5/4325; A61B 5/4381; A61B 5/444; A61B 10/0041; A61B 2505/05; A61K 49/0032; A61K 49/0056
USPC .......................................................... 600/431
See application file for complete search history.

(56) References Cited

FOREIGN PATENT DOCUMENTS

| WO | 2009107139 A1 | 9/2009 |
|---|---|---|
| WO | WO2010-076334 A2 | 7/2010 |
| WO | WO2010-106169 A1 | 9/2010 |

OTHER PUBLICATIONS

Choi, Hak Soo, etal. "Targeted zwitterionic near-infrared fluorophores for improved optical imaging." Jan. 6, 2013. Nature Biotechnology. vol. 31. 148-153 (Year: 2013).*
Conti, Laura, et al. "Optical imaging detection of microscopic mammary cancer in ErbB-2 transgenic mice through the DA364 probe binding avB3 integrins." Jun. 5, 2012. Contrast Media & Molecular Imaging. vol. 8 Issue 4. 350-360. (Year: 2013).*
Belvisi, Laura et al., "Biological and molecular properties of a new [alpha]V[beta]3/[alpha]V[beta]5 integrin antagonist", Molecular Cancer Therapeutics, 2005, 4(11), pp. 1670-1680, mct.aacrjournals.org, American Association for Cancer.
Choi, Hak Soo et al., "Targeted zwitterionic near-infrared fluorophores for improved optical imaging", Nature Biotechnology, 2013, vol. 31, No. 2, pp. 148-153, with "Online Methods", one page; and Supplementary Information, XP055193916, ISSN: 1087-0156, DOI: 10.1038/nbt.2468, Nature America, Inc.
Connors, Kenneth A., Binding Constants, The Measurement of Molecular Complex Stability, Chapter 4, 1987, pp. 141-161, John Wiley & Sons, New York.
Conti, Laura et al., "Optical imaging detection of microscopic mammary cancer in ErbB-2 transgenic mice through the DA364 probe binding [alpha]V[beta] 3 integrins", Contrast Media & Molecular Imaging, 2013, vol. 8, No. 4, pp. 350-360, XP055193763, ISSN: 1555-4309, DOI: 10.1002/cmmi.1529.
Gioux, Sylvain et al., "Image-Guided Surgery using Invisible Near-Infrared Light: Fundamentals of Clinical Translation", Molecular Imaging, 2010, 9(5): 237-255, doi:10.2310/7290.2010.00034, BC Decker Inc.
Humblet, Valerie et al., "High-affinity Near-infrared Fluorescent Small-molecule Contrast Agents for In Vivo Imaging of Prostate-specific Membrant Antigen", Molecular Imaging, 2005, vol. 4, No. 4, pp. 448-462, Neoplasia Press, Inc.
Humblet, Valerie et al., "Multivalent Scaffolds for affinity Maturatino of Small Molecule Cell Surface Binders and Their Application to Prostate Tumor Targeting", Journal of Medicinal Chemistry, 2009, vol. 52, No. 2, pp. 544-550, American Chemical Society.
Lanzardo, Stefania et al., "A new optical imaging probe targeting [alpha]V[beta]3 integrin in glioblastoma xenografts", Contrast Media & Molecular Imaging, 2011, vol. 6, No. 6, pp. 449-458, XP055193745, ISSN: 1555-4309, DOI: 10.1002/cmmi.444.
Manzoni, Leonardo et al., "Cyclic RGD-Containing Functionalized Azabicycloalkane Peptides as Potent Integrin Antagonists for Tumor Targeting", ChemMedChem, 2009, vol. 4, pp. 615-632, Wiley-VCH Verlag GmbH & Co., Weinheim, www.chemmedchem.org.
Pawlik, Timothy M. et al., "Effect of Surgical Margin Status on Survival and Site of Recurrence After Hepatic Resection for Colorectal Metastases", Annals of Surgery, 2005, vol. 241, No. 5, pp. 715-724, Lippincott Williams & Wilkins.
Pisano, Marina et al., "In Vitro Activity of the αVβ3 Integrin Antagonist RGDechi-hCit on Malignant Melanoma Cells", Anti-cancer Resarch, 2013, vol. 33, pp. 871-879.
Pontes-Junior, Jose et al., "Association Between Integrin Expression and Prognosis in Localized Prostate Cancer", The Prostate, 2010, 70:1189-1195, Wiley-Liss, Inc.
Schaafsma, Boudewijn E. et al., "The Clinical Use of Indocyanine Green as a Near-Infrared Fluorescent Contrast Agent for Image-Guided Oncologic Surgery", Journal of Surgical Oncology, 2011, 104:323-332, Wiley-Liss, Inc.
Schmidt, Michael M. et al., "A modeling analysis of the effects of molecular size and binding affinity on tumor targeting", Molecular Cancer Therapeutics, 2009, 8:2861-2871, American Association for Cancer Research, downloaded from mct.aacrjournals.org.
Siegel, Rebecca et al., "Cancer Treatment and Survivorship Statistics, 2012", CA Cancer J Clin, 2012, 62:220-241, American Cancer Society.
Sutherland, Mark et al., "RGD-Binding Integrins in Prostate Cancer: Expressio Patterns and Therapeutic Prospects against Bone Metastasis", Cancers, 2012, vol. 4, pp. 1106-1145, doi:10.3390/cancers4041106, ISSN 2072-6694, www.mdpi.com/journal/cancers.
Terwisscha van Scheltinga, Anton G.T. et al., "Intraoperative Near-Infrared Fluorescence Tumor Imaging with Vascular Endothelial Growth Factor and Human Epidermal Growth Factor Receptor 2 Targeting Antibodies", The Journal of Nuclear Medicine, 2011, vol. 52, No. 11, pp. 1778-1785, doi:10.2967/jnumed.111.092833, the Society of Nuclear Medicine, Inc.
Toyohara, Jun et al., "Animal tumor models for PET in drug development", Ann Nucl Med, 2011, vol. 25, No. 10, pp. 717-731, Springer, doi:10.1007/s12149-011-0531-x.
Verbeek, Floris P.R. et al., "Near-Infrared Fluorescence Imaging of Both Colorectal Cancer and Ureters Using a Low-Dose Integrin Targeted Probe", Annals of Surgical Oncology, 2014, total page count: 10, doi:10.1245/s10434-014-3524-x, Society of Surgical Oncology.
Wu, Jason et al., "Near-infrared fluorescence and nuclear imaging and targeting of prostate cancer", Translational Andrology and Urology, 2013, vol. 2, No. 3, pp. 254-264, AME Publishing Company, www.amepc.org/tau.
Zaminer, Jan et al., "Addressing Protein-Protein Interactions with Small Molecules: A Pro-Pro Dipeptide Mimic with a PPII Heix Conformation as a Module for the Synthesis of PRD-Binding Ligands", Angewandte Chemie International, 2010, vol. 49, pp. 7111-7115, Wiley-VCH Verlag GmbH & Co., Weinheim., www.angewandte.org.
European Search Report for European application No. 14199240.4 , dated Jun. 12, 2015.
International Search Report and Written Opinion for PCT application No. PCT/EP2015/080545, dated Mar. 8, 2016.

* cited by examiner

INTRA-OPERATIVE IMAGING

CROSS-REFERENCE TO RELATED APPLICATIONS

This application is the national stage application of corresponding International Application Number PCT/EP2015/080545, filed Dec. 18, 2015, which claims priority to and the benefit of European Application Number EP14199240.4, filed Dec. 19, 2014, all of which are hereby incorporated by reference in their entirety.

FIELD OF THE INVENTION

The present invention relates to the field of the in vivo intra-operative imaging. More particularly, the invention relates to the use of the Near Infra-Red (NIR) fluorescent probe DA364 comprising an aza-bicycloalkane based cyclic peptide labelled with a Cy5.5 dye moiety in the guided surgery of tumors and pathologic regions. The invention further relates to an optical imaging method that comprises using this fluorescent probe in the intraoperative imaging, for the identification and demarcation of tumor margins during thereof surgical resection.

STATE OF THE ART

Considerable efforts have been devoted in the last decades to the development of improved therapeutic modalities, such as targeted chemotherapy and radiotherapy, for the treatment of acute diseases and cancers. However, curative surgery still is the treatment of choice for most cancers, especially for malignancies at early stages, and the surgical resection is currently the standard of care for the treatment of the majority of cancer patients (CA Cancer J. Clin. 2012; 62:220-241). For example, 93% of patients with breast cancer at an early stage (I and II) and 75% of those who are in a later stage (III and IV) are treated surgically; surgery to remove the cancer and nearby lymph nodes is the most common treatment for early stage (stage I and II) colon (94%) and rectal (74%) cancer. A colostomy is more commonly used for rectal cancer (26%) than for colon cancer (7%). Radical prostatectomy is the treatment of choice for 57% of patients with prostate cancer between the ages of 18 and 64 years and 33% of patients aged from 65 to 74.

Despite major advancements in preoperative imaging techniques and postoperative associated treatments, the patient prognosis is essentially associated with success of the original surgery, namely with the complete surgical removal of the cancerous tissues and cells. Therefore, critical to the success of the surgical treatment and patient survival is the clear identification and demarcation of tumor margins helping the surgeon to avoid removing or injuring healthy tissues, and, especially, not to leave residual tumor cells leading to the formation of local recurrences, with often serious or fatal effects (Ann Surg 2005; 241: 715-724).

At present, most of oncologic surgery is performed under the only guide provided by the surgeon direct visual inspection and palpation, where the surgeon's experience and his ability to discriminate pathologic tissues from normal tissue are the only available guides in the choice of tissues to be resected. However, cancer tissues are often difficult to be distinguished from peritumoral edema or inflammation by a human eye, or are too small to be felt with hands. Additional difficulties then arise from marked differences existing among tumor types and oncologic patients, and the consequent lack of surgical protocols.

An increasing interest, therefore, exists in the development of imaging technologies and probes consenting to increase the surgeon's ability to "see" tumor margins and thus improve surgical outcomes.

Over the past several years the use of integrated fluorescence light and standard white light has entered the surgical theatre, demonstrating to allow the differentiation between healthy and pathological tissues, especially when coupled with near-infrared (NIR) fluorophores targeted to the pathological area. Advantages of the NIR fluorescent light, acting within the NIR window of 700-900 nm, include a tissue penetration from millimetres to centimetres, reduced scattering and autofluorescence maximizing the signal to background contrast provided by exogenous NIR contrast agents. Moreover, the NIR fluorescence imaging affords the surgeon advantages such as real time visualization, non-contact imaging, lack of ionizing radiation and unaltered look of the surgical field of view. To this extent, in fact, only the activation of a specific intraoperative imaging system allows the surgeon to "see" the contrast agent that would, otherwise, be invisible to the human eye, thereby avoiding contamination of the clinical picture observed by the surgeon (Mol Imaging. 2010; 9(5): 237-255).

An increasing interest has been then devoted to NIR fluorescent imaging probes maximizing the signal to background ratio (SBR) recorded at the tumor site and enabling the identification and demarcation of the tumor area of interest.

Integrins, especially $\alpha_v\beta_3$ and $\alpha_v\beta_5$, are transmembrane cell surface proteins expressed by most cell types that are known to be upregulated on activated endothelial cells during neovascularization of several malignancies, e.g. including melanoma, glioblastoma, ovarian, breast, lung, liver and colon cancer, where they play an important role in the early phase of tumor angiogenesis, and in processes governing tumor growth and metastasis (Mol. Cancer Ther. 2005; 4:1670-1680). As such, they constitute an attractive target for NIR fluorescent probes tumor targeted. Indeed, the majority of the tumor targeted probes currently under study includes in their structure a RGD-based integrin targeted moiety aimed at accumulating the fluorescent probe at the targeted tumor site.

Integrin targeted diagnostic agents for medical imaging, including optical imaging, are, for instance, disclosed in WO2006/095234.

The NIR fluorescent probe including an aza-bicycloalkane based cyclic peptide labelled with a Cy5.5 dye which is identified as DA364, and has the following formula

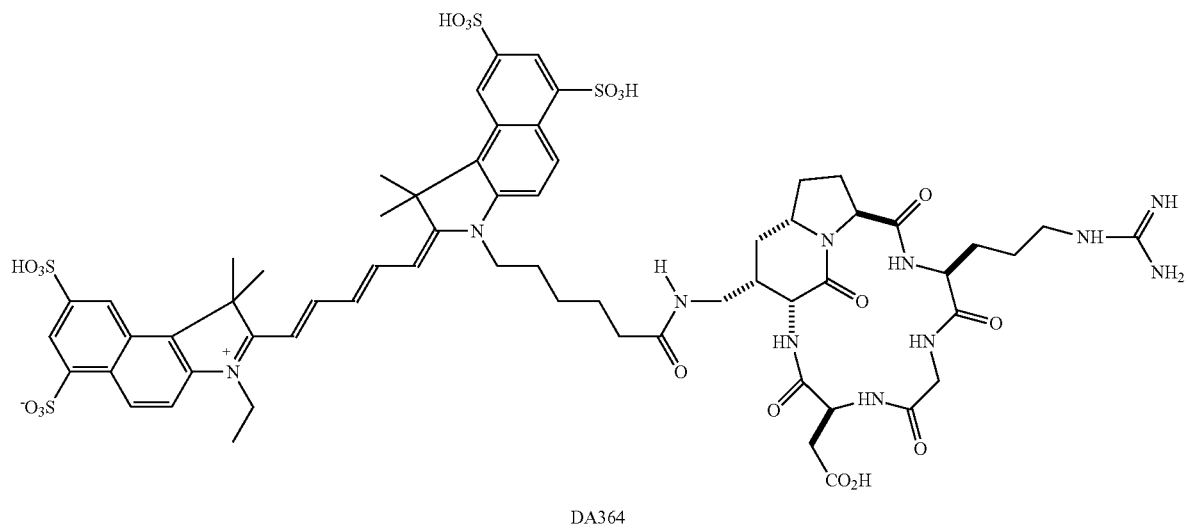

DA364 and its use for the optical imaging detection of $\alpha_v\beta_3$ integrin in glioblastoma xenografts and for the early diagnosis of breast cancer are disclosed in Contrast Media & Molecular Imaging 2011; 6:449-458 and Contrast Media & Molecular Imaging 2013; 8, 350-360, respectively.

Zwitterionic NIR fluorophores and integrin targeted RGD-derivatives thereof are disclosed in Nature Biotechnology 2013; 31(2), 148-153 and in the cited literature, and their use in the Near-Infrared fluorescence imaging of both colorectal cancer and ureters has been recently disclosed in Ann. Surg. Oncol. 2014 Feb. 11. (published online, ahead of print). These fluorescent probes have been specifically engineered for providing an optimized signal to background (non-tumor) ratio (SBR) and, thus, an optimal visualization and demarcation of those peculiar tumors having marked $\alpha_v\beta_3$ integrin overexpression.

Prostate cancer-targeted NIR fluorescent agent have also been disclosed comprising a NIR fluorophore conjugated to a peptide or a small targeting molecule accumulating the fluorescent probe to the targeted tumor site through binding interaction with the prostate-specific membrane antigen (PSMA) (see, for instance Mol. Imaging 2005; 4(4), 448-462 and cited literature).

Tumor-specific NIRF contrast agents have also been obtained by conjugation of NIR fluorophores to FDA approved and clinically available monoclonal antibodies or FABs (e.g. bevacizumab or cetuximab) or peptides (see, for instance, J. Nucl. Med. 2011; 52:1778-1785).

Optical imaging agents comprising conjugates of near-infrared dyes with synthetic polyethyleneglycol (PEG) polymers are disclosed in WO2010/106169 and the cited literature.

A possible limitation to the use of these macromolecular probes in the intraoperative imaging is, however, represented by their large dimension, that typically significantly increases their persistence in the circulation before a complete clearance from the blood system (Mol. Cancer Ther. 2009; 8:2861-2871, and Trends in Pharmacological Sciences Vol. 29 No. 2).

Functionalized RAFT (Regioselectively Addressable Functionalized Template) scaffolds (RAFT) grafted to $\alpha_v\beta_3$ integrin targeting motifs on one of the faces and to cyanine markers on the other face and their use in the intraoperative detection of tumor margins are disclosed in WO2010/076334.

Main limitation to the development of the NIR fluorescence guided surgery, however, lies in proven obstacles encountered in translating NIR agents for fluorescent optical imaging into intraoperative clinical application and in the poor availability of validated NIR fluorescent probes.

Indeed, a diagnostic imaging procedure requires that, in a time window compatible with patient imaging, the fluorescent contrast agent preferentially accumulates at a pathological site and locally produces a signal significantly higher than that observed in the surrounding healthy tissue (and which is not attenuated or scattered by the living tissue). To this end, it is quite irrelevant whether the signal is generated by a contrast agent bound to the targeted tumor moiety or still circulating, at least partially, in the upregulated tumor vascularization. Therefore, the complete elimination of the unbound probe from the circulation is not a need in the NIR fluorescent diagnostic imaging. Likewise, for diagnostic purposes, it is not necessary that the SBR remains optimal for long times, such as those of the surgery.

In the case of guided surgery, the preferential accumulation of the NIR fluorescent probe at the tumor site of interest is a necessary condition, but is not sufficient.

A NIRF contrast agent for use in guided surgery must display a concentration difference of the fluorescent probe between healthy and pathologic tissue clear, precise, and persistent, so as to ensure a clear and sharp demarcation of tumor margins for the whole duration of the surgical tumor resection. At the same time, it is absolutely necessary that the circulating (unbound) fluorescent probe is completely cleared from the blood system before surgery, so as to avoid that any residual contrast agent released with bleeding (produced during the surgery) can contaminate the surgical theatre and confuse the surgeon visual field.

To achieve these results, a suitable NIR fluorescent agent for use in the imaging-guided surgery must display:
optimal permanence time in the blood system, long enough to ensure a sufficient contact time of the agent with the target (and, hence, its effective accumulation at the target site) and, at the same time, the complete elimination of the unbound agent from the circulating system;
a selective accumulation at the targeted tumor site, including both a selective uptake and homogeneous distribution of the agent into the pathologic area, and a sufficient retention (at the tumor site) consenting the clear demarcation of the whole tumor region throughout the duration of the surgery;

a slow release kinetics and a negligible extraction and diffusion (of the fluorescent agent) from the pathologic area towards the healthy tissue, so as to prevent the contamination of tumor margins or compromising the recognition of infiltrating tissues; in addition the fluorescent probe must provide a signal which is not bleached or compromised owing to a prolonged exposition to the excitation light.

Of critical importance, therefore, are the rate of clearance and the route of clearance of the NIR agent, since they control the blood half-life and, hence, the contact time with the target of interest, and further influence the background signal in the excretion organs. Equally relevant is the affinity displayed by the NIR probe for the target, which has to be almost absolute, or fully compatible with any existing non-specific uptake.

Further difficulties can then arise from the expression, both in terms of abundance and uniformity of distribution of the targeted receptors or epitopes in the tumor of interest, both of which are strongly dependent on the type of tumor, the patient, and the effect promoted by any optional therapeutic pre-treatments, for instance carried out to reduce the tumor mass before surgery.

In fact, the over-expression of some typical tumor receptors, for instance integrins, may decrease or be modified by effect e.g. of chemotherapeutic treatments so as to compromise the effective accumulation of probes specifically targeted to these receptors in pre-treated tumors or metastases, and, in turn, their ability to provide a reliable demarcation thereof.

Finally, the misleading effects caused by the different optical properties of different tissues can impede or reduce the ability of a contrast agent to differentiate between areas of healthy and tumor tissues especially for the agents operating out of the tissue optical window (NIR) such as fluorescein and 5-ALA. This limitation is worsened particularly at the tumor margins where the fluorescent signal can be low.

The multiplicity and complexity of all the above factors is probably the reason behind the fact that, although a variety of new fluorophores and tumor-specific NIR fluorescent agents have been developed and tested in preclinical studies, either exploiting a specificity for tumor receptors or a specificity for tumor angiogenetic markers, none of them has already obtained a clinical approval.

Indeed, the only FDA approved NIR fluorescent contrast agents are methylene blue (MB) and indocyanine green (ICG) which remains, this latter, the reference product in the current clinical practice. None of them is tumor targeted.

Therefore a need exists for tumor-specific NIR fluorescent probes and intraoperative imaging modalities enabling the surgeon with a real-time detection of tumor margins and facilitating the radical and precise resection of the pathological areas.

SUMMARY OF THE INVENTION

As mentioned above, the use of the NIR fluorescent agent identified as DA364, and having the above depicted formula, for the optical imaging of tumors highly over-expressing $\alpha_v\beta_3$ integrins was known in the diagnostic field from the above cited literature.

We have now found that this compound can be effectively used in the intraoperative imaging to provide a real-time detection and demarcation of tumor margins during the NIR-fluorescence imaging guided curative surgery of tumors. The use of DA364 may thus help the surgeon in reducing the risk of leaving residual tumor tissue or unnecessarily removing large portions of healthy tissues (with the associated risk of possibly injuring local innervation and vascularization.

Moreover, it has been observed that this agents provides an optimal accumulation and retention at the tumor site, thus enabling a clear identification and demarcation of tumor margins, even of tumors having a reduced integrin overexpression.

Accordingly, in general terms the present invention relates to the use of fluorescent probe DA364 in the intraoperative imaging, and, more particularly, in tumor surgery, to provide the surgeon with a real-time detection and demarcation of tumor margins.

More particularly, in one aspect the invention relates to the use of DA364 in surgery, particularly in the NIR fluorescence-guided curative surgery of a tumor or pathologic area in a patient, for the intraoperative detection and demarcation of the margins of the pathological area or tumor region to be excised.

In another aspect the invention relates to a composition comprising the NIR Fluorescent contrast agent known as DA364 for use in the intraoperative imaging, for the real-time identification and demarcation of tumor margins.

In a further aspect the invention provides an intraoperative imaging method that comprises using DA364 as a contrast agent to identify and demarcate the margins of the tumor undergoing curative surgery.

In a still further aspect the invention relates to a guided-surgery protocol for the curative surgery of a tumor mass, area or region in a patient that comprises using DA364 and fluorescent light for the intraoperative or per-operative delimitation and demarcation of tumor margins.

In certain embodiments, said intra- or pre-operative imaging is performed on a tumor having a reduced over-expression of $\alpha_v\beta_3$ integrin.

In other embodiments, said intra- or per-operative imaging is performed on a tumor having a variable over-expression of $\alpha_v\beta_3$ integrin.

DETAILED DESCRIPTION OF THE INVENTION

To provide a useful support to a surgeon, an effective contrast agent for use in guided surgery shall be capable of selectively accumulate at the pathologic site of interest in a substantially homogeneous manner, in order to provide a clear detection of the whole tumor area and a sharp and persistent demarcation of its borders.

The contrast agent DA364, has proven to ensure optimal accumulation and retention at the tumor site and then locally provide a persistent fluorescent signal enabling the surgeon to "see" in real-time, during the curative surgery, the pathological area to be excised and to unambiguously identify the surgical margins thereof. Interestingly, in fact, this compound shows a pharmacokinetic profile and pharmacodynamics properties allowing it to stay in the circulating system a time long enough to guarantee its selective and substantially homogeneous accumulation at the site of interest before its complete elimination from circulation.

It has further been observed that the compound DA364 unexpectedly provides an effective accumulation and retention at tumor sites for tumors having a reduced (e.g. limited or inhomogeneous) $\alpha_v\beta_3$ integrin over-expression.

While not willing to be bound to any particular theory, it may be hypothesized that the accumulation at the tumor site (in particular with reduced or inhomogeneous over-expression of $\alpha_v\beta_3$ integrin) is the result of the combined effect of both a high specificity for integrin receptors, especially $\alpha_v\beta_3$, and a non-specific retention, e.g. mediated by non-specific binding interactions with extracellular components, for instance including extravascular plasma albumin leaked from injured tumor vasculature.

This unexpected ability to enter and effectively distribute in the extracellular (interstitial) space of the tumor region contributes, from one side, to amplify and to make more persistent the signal recorded at the tumor site, which is in fact determined by both the NIR agent bound to the $\alpha_v\beta_3$ integrin receptors expressed on tumor and endothelial cells (specific binding) and the agent retained in the interstitial spaces of the tumor as a result of non-specific interactions (non-specific binding).

Advantageously, moreover, the optimal accumulation and retention at the tumor site enable this agent to provide an improved and persistent demarcation of tumor margins even in the presence of pathological tissues having a reduced or non-homogeneous integrin expression, and to overcome the limitations arising from the variability of integrins expression in the individual tumors and in the individual patients.

In fact, the contribution to the detected signal provided by the fluorescent probe retained in the extracellular space of the tumor has advantageously proven to compensate for any reductions or non-homogeneity of the fluorescent signal, and any subsequent inaccurate or ambiguous demarcation of tumor margins, possibly caused by a reduced or non-homogeneous expression of the specifically targeted integrin receptors.

Advantageously, therefore, besides providing a real-time improved NIR fluorescent demarcation of tumors and pathologies having a marked expressing of $\alpha_v\beta_3$ integrin receptors, DA364 has proven to provide a reliable demarcation of the borders of vascularized tumors and pathologic areas that, either because of their specific nature or because of the effect promoted by previous therapeutic treatments display, or could display, a limited or non-homogeneous expression of $\alpha_v\beta_3$ integrin receptors.

As a result, the NIR agent of the invention can advantageously be considered of general use, namely it can be proposed for use in the NIR fluorescence-guided curative surgery of a patient, to provide the surgeon with a real-time reliable identification and demarcation of the margins of the malignant region to be resected, regardless of any possible reduced or inhomogeneous expression of $\alpha_v\beta_3$ integrin receptors it may displays.

An embodiment of the present invention therefore relates to the use of the contrast agent DA364 in the intraoperative imaging of a patient, for the real-time detection and demarcation of tumor margins.

In a preferred aspect, the said intraoperative imaging is recorded directly during the curative surgery, in particular during a curative tumor surgery, to provide the surgeon with a real-time identification of the margins the tumor area or malignant region to be removed.

A preferred embodiment of the invention, therefore, relates to the use of the contrast agent DA364 in surgery, and, preferably, in the guided surgery of a tumor, to provide a real-time identification and demarcation of the margins of the pathologic area to be removed.

The curative surgery according to the invention, which comprises using DA364 as contrast agent to detect and demarcate the tumor region of interest, is suitably carried out under fluorescence light, for instance obtained by using an excitation light suitably filtered in the wavelength range e.g. of from about 600 to about 700 nm. According to a particularly preferred embodiment, the invention relates to the use of the contrast agent DA364 in NIR fluorescence-guided tumor surgery, to provide the intraoperative, real time detection and demarcation of the borders of the pathological area or region to be excised.

In the present description and claims, the terms "tumor", "pathological area", "malignancy", or "malignant area or region", as used herein interchangeably, refer to a tissue, organ, area or region of the individual patient's body which comprises tumor cells, regardless of their quantity and distribution, thus including tumors, metastasis and infiltrated body region or tissues, while "healthy area, tissue or region" is the tissue, area or region of the individual patient's body that does not include any tumor cell.

The terms tumor "margins" or "borders", as used herein, refer to that region of the tumor or other malignancy that demarcates and separates the pathologic from healthy area.

The expressions "surgical margins" or "tumor free margin" as used herein refer to excision margins followed by the surgeon in the surgical resection of the tumor that include the pathologic region up to its visible (e.g. by NIR fluorescent light) border, and an additional unaffected (i.e. non-fluorescent) extra-region around the detectable tumor border, typically of at least 3 mm, and preferably of at least about 5 mm up to about 1 cm and more than 1 cm.

The terms "patient" or "individual patient" as used herein comprise an animate subject, preferably a mammalian subject, and, more preferably a human being suffering for a tumor or a malignant disease treatable by surgery.

The expression "tumor with reduced expression of $\alpha_v\beta_3$ integrin receptors" refers to tumors showing an over-expression of $\alpha_v\beta_3$ integrin receptors which, while been higher than the expression of $\alpha_v\beta_3$ integrin receptors in normal healthy tissue, is generally reduced with respect to the expression of $\alpha_v\beta_3$ integrin receptors in tumors know to have an important over-expression of said receptors.

The reduced over-expression may be due either to an effective lower (limited) expression of $\alpha_v\beta_3$ integrin receptors by the tumor cells or to an inhomogeneous distribution of an (otherwise relatively high) expression of $\alpha_v\beta_3$ integrin receptors in the tumor mass, for instance when the $\alpha_v\beta_3$ integrin is expressed by endothelial cells associated to neoangiogenis, or to a combination of both. In this latter case, the measure of the of $\alpha_v\beta_3$ integrin expression with respect to the total mass of the tumor will thus provide the effective expression $\alpha_v\beta_3$ integrin in the tumor mass, independently from the specific expression of $\alpha_v\beta_3$ integrin of tumor cells in the tumor mass.

As observed by the applicant, the amount of $\alpha_v\beta_3$ integrin expression in a tumor mass may be determined according to know analytical techniques such as, for instance, the western blot analysis that allows the quantification of the content of a specific protein in tissues, as described in detail in the experimental part.

According to this technique, it is possible to determine the amount of $\alpha_v\beta_3$ integrin (in ng) expressed per mg of tumor mass or preferably per μg of the total protein lysate in the tumor mass (to have a better normalization on the number and kind of cells). In this manner, it is not relevant whether the reduced is due to an effective lower $\alpha_v\beta_3$ integrin expression of the tumor cells or to an inhomogeneous distribution within the tumor mass of otherwise high $\alpha_v\beta_3$ integrin expressing cells; the measured value provides in fact an indication of the $\alpha_v\beta_3$ integrin expression in the total tumor mass.

In particular, it has been determined that for tumors with high $\alpha_v\beta_3$ integrin over-expression (e.g. malignant melamoma type IV or U-87 MG tumor), the amount of $\alpha_v\beta_3$ integrin is higher than 0.20 ng/µg of total proteins (about 0.241149 and 0.221000 ng of $\alpha_v\beta_3$ integrin/µg proteins). On the other side, it has been observed that the DA364 imaging agent is surprisingly suitable for the visualization (and thus also for a method for the intra- or per-operatory surgery) of tumors with reduced expression of $\alpha_v\beta_3$ integrin receptors. In particular, DA364 is suitable for visualizing tumors showing an expression of 0.15 ng of $\alpha_v\beta_3$ integrin/µg proteins or less, of 0.10 ng of $\alpha_v\beta_3$ integrin/µg proteins or less, or of 0.05 ng of $\alpha_v\beta_3$ integrin/µg proteins or less; and down to e.g. 0.005 ng of $\alpha_v\beta_3$ integrin/µg proteins, 0.01 ng of $\alpha_v\beta_3$ integrin/µg proteins or 0.02 ng of $\alpha_v\beta_3$ integrin/µg proteins.

Alternatively defined as an expression ratio, the DA364 is suitable for visualizing tumors showing an expression of $\alpha_v\beta_3$ integrin of 60% or less with respect to the $\alpha_v\beta_3$ integrin expression in a malignant melamoma type IV (CP565523 from OriGene), of 40% or less or of 20% or less; and down to e.g. 2%, 4% or 8% the $\alpha_v\beta_3$ integrin expression in a malignant melanoma type IV.

As known in the art, many tumors (or cells in tumor mass) may show a variable expression of $\alpha_v\beta_3$ integrin during their different development phases, tipically showing an increase of $\alpha_v\beta_3$ integrin expression in the progression from earliest to later tumor stages.

As observed by the Applicant, the advantageous property of visualizing tumors with relatively low expressions of $\alpha_v\beta_3$ integrin also allows using the DA364 agent for the visualization (including intraoperatory and peroperatory visualization) of those tumors having a variable expression of $\alpha_v\beta_3$ integrin during their respective development or progression phases.

In particular, tumors at a relatively early development phase (having a relatively reduced over-expression of $\alpha_v\beta_3$ integrin with respect to a higher over-expression at later development phases) may advantageously be visualized, specifically during the surgery.

Thus a further embodiment of the invention relates to a method for the intra- or per-operatory visualization of tumors with variable expression of $\alpha_v\beta_3$ integrin wherein said tumor has a development phase during which the expression of $\alpha_v\beta_3$ integrin is of 0.15 ng of $\alpha_v\beta_3$ integrin/µg proteins or less, of 0.10 ng of $\alpha_v\beta_3$ integrin/µg proteins or less, or of 0.05 ng of $\alpha_v\beta_3$ integrin/µg proteins or less; and down to e.g. 0.005 ng of $\alpha_v\beta_3$ integrin/µg proteins, 0.01 ng of $\alpha_v\beta_3$ integrin/µg proteins tumors or 0.02 ng of $\alpha_v\beta_3$ integrin/µg proteins.

According to an alternative embodiment, the invention relates to a method for the intra- or per-operatory visualization of tumors with variable expression of $\alpha_v\beta_3$ integrin wherein said tumor has a development phase during which the expression of $\alpha_v\beta_3$ integrin is of 60% or less with respect to the $\alpha_v\beta_3$ integrin expression in a malignant melamoma type IV (CP565523 from OriGene), of 40% or less or of 20% or less; and down to e.g. 2%, 4% or 8% the $\alpha_v\beta_3$ integrin expression in a malignant melanoma type IV.

In one embodiment of the invention the tumor or malignancy under curative surgery is selected from the group consisting of melanoma, glioma, glioblastoma, neuroblastoma, sarcoma, cancer of the ovary, breast, lung, liver, colon, head-neck and prostate; preferably, is selected from glioma, glioblastoma, cancer of the breast, ovary and prostate, this last being particularly preferred.

In a further embodiment the invention relates to a pharmaceutical diagnostic composition comprising an effective amount of DA364 for use in the intraoperative and per-operative (or perioperative, as herein used interchangeably to indicate the time period describing the duration of a patient's surgical procedure) imaging, for the real-time detection and demarcation of tumor margins in a patient in the whole time period of the surgical procedure.

To this extent, the intraoperative or per-operative (or perioperative, as herein used interchangeably to indicate the time period describing the duration of a patient's surgical procedure) imaging according to the invention belongs to the optical imaging, which is preferably carried out in the fluorescent optical range, more preferably with a NIR fluorescent light.

In a preferred embodiment the invention relates to a pharmaceutical diagnostic composition comprising an effective amount of DA364 for use in the guided surgery and, preferably, in the NIR fluorescent-guided surgery of an individual patient tumor, for the real-time detection and demarcation of the margins of the pathologic area to be resected.

To this extent, and unless otherwise provided, the term "effective amount" or "effective dose", as used herein, refers to any amount of the NIR agent DA364 that is sufficient to fulfil its intended diagnostic purpose(s): i.e., for example, to provide in real-time, namely during the fluorescent-guided surgery of an individual patient, and for all the duration of the surgery, a clear detection and demarcation of the borders of tumor areas, regions, or tissues, and malignant infiltrations to be resected. For instance, a suitable dose may range from about 0.6 to about 250 nmol of fluorescent probe per kg of the individual patient and, preferably, is from 1 to 60 and, more preferably, from 1.7 to 17 nmol/kg, corresponding to a dose of from about 0.05 to 20.0 mg and, preferably, from 0.08-5.0 mg and, most preferably, from 0.15 to 1.5 mg of fluorescent probe per patient.

A suitable pharmaceutical composition according to the invention may be formulated in accordance with routine procedures as a pharmaceutical composition appropriate for all commonly used administration routes. Typically, the composition comprises an effective amount of the NIRF contrast agent and at least one suitable carrier. Non limiting examples of pharmaceutically acceptable carriers include sterile water, saline solution, buffered saline water, buffered saline solution (including buffers like phosphate or acetate), alcohol, vegetable oils, polyethylene glycols, gelatin, lactose, amylose, magnesium stearate, talc, silicic acid, paraffin, etc. Where necessary, the composition may also include a solubilizing agent and a local anaesthetic such as, e.g., lidocaine to ease pain at the site of the injection; and further may include preservatives, stabilizers, wetting agents, emulsifiers, salts, lubricants, etc. as long as they do not react deleteriously with the active compounds. Similarly, the composition may comprise conventional excipients, i.e., pharmaceutically acceptable organic or inorganic carrier substances suitable for parenteral, enteral or intranasal application which do not deleteriously react with the active compounds. Generally, the ingredients will be supplied either separately or mixed together in unit dosage form, for example, as a dry lyophilized powder or water free concentrate in a hermetically sealed container such as, e.g., an ampoule or sachette indicating the quantity of active agent in activity units. Where the composition is to be administered by infusion, it can be dispensed with an infusion bottle containing sterile pharmaceutical grade "water for injection" or saline. Where the composition is to be administered by injection, an ampoule of sterile water for injection or saline may be provided so that the ingredients may be mixed prior to the administration.

Where the composition is intended for oral administration, it can be suitably formulated for example as a tablet, a capsule or a pill, or as a liquid or a suspension for oral use.

In a preferred aspect, pharmaceutical compositions of DA364 according to the invention are properly formulated in isotonic sterile aqueous, optionally buffered, solutions for parenteral administration, and most preferably for intravenous or intra-arterial administration.

Preferably, the said diagnostic composition has a concentration of the NIR agent DA364 of at least 0.05 mg/mL, and more preferably of from 0.15 to 40 mg/mL and is supplied, for instance as a bolus, or as two or more doses separated in time, or as a constant or non-linear flow infusion.

The invention moreover relates to a method for the optical imaging of the margins of a pathologic area and, especially of a tumor of an individual patient that comprises using DA364 to generate the imaging and the demarcation of the margins of the tumor. Preferably the optical imaging is fluorescence-based and, more preferably, is a NIR fluorescence-based optical imaging and includes detecting and demarcating the borders of the tumor of interest under fluorescent light.

In one embodiment, the optical imaging is carried out in-vitro (ex-vivo), on the resected tumor or portions of the tumor, e.g. tissue samples obtained from a surgical removal of a tumor of an individual patient, and comprises examining under fluorescent light excised samples and detecting the fluorescent signal they provide, in order to identify the margins of the removed tumor and verify the presence of a non-fluorescent area around them. To this extent, the examined ex vivo tumor samples may be obtained from a tumor resected from an individual patient suitably pre-treated with DA364. Alternatively, the optical imaging is carried out in-vitro (ex-vivo), on tumor or portions of the tumor resected from an untreated patient, wherein, in this case, the agent of the invention is used as an histological marker of the tumor margins.

More preferably, the optical imaging of tumor margins is carried out in vivo, during the intraoperative surgical inspection of a pathologic body area of an individual patient including the tumor of interest.

Accordingly, preferred further aspect of the present invention relates to the use of contrast agent DA364 in a method for the in vivo detection of the margins of an alleged tumor in a patient to whom DA364 has been previously administered, said method comprising:

i) generating an intraoperative optical imaging of a a region of interest (ROI) in comprising said alleged tumor, and ii) detecting the margins of the alleged tumor under fluorescent light.

In one embodiment, the above method further comprises administering an effective amount of the DA364 fluorescent probe to the patient and allowing it to circulate in the patient's body for an appropriate time before imaging.

In a preferred embodiment, the method is carried out in vivo, and comprises generating the intraoperative imaging and the determining the demarcation of the tumor margins in a patient having been pre-administered with a suitable amount of the fluorescent contrast agent DA364, at an appropriate time window preceding the intraoperative imaging.

According to a preferred implementation, the intraoperative optical imaging of the tumor region and the detection of the margins of the tumor are carried out by illuminating the ROI by means of a suitably spectrally resolved (typically suitably filtered), continuous or discontinuous, excitation light source capable of exciting the DA364 agent, and then detecting the fluorescent light emitted by the contrast agent by using an appropriate fluorescence detector, allowing to filter and separate the emitted fluorescent signal. To this extent, non-limiting examples of equipment and devices to implement the above steps are e.g. disclosed in Mol. Imaging 2010 October; 9(5): 237-255, and the cited literature.

A fluorescent image of the ROI is thus obtained under fluorescent light, reflecting the selective accumulation of the DA364 probe at the tumor site of interest, which enables a clear and unambiguous demarcation of tumor borders.

The intraoperative optical imaging of the tumor region and the detection of the margins of the tumor may advantageously be carried out in real-time, during the surgical inspection and curative resection of a pathologic body region or area and, especially, of a tumor, to enable the surgeon to "see" the tumor of interest and to clearly identify the margins of the tumor area to be excised and to assist him (her) in the resection of the tumor from an individual patient.

A further aspect of the present invention therefore relates to a method for the guided surgery of a tumor of an individual patient which comprises, as main steps:

i) providing the individual patient with an appropriate amount of the fluorescent probe DA364;

ii) generating an intraoperative fluorescence-based optical imaging of a region of interest comprising the alleged tumor under curative surgery;

iii) identifying the margins of the tumor under fluorescent light, and iv) operating the curative surgery of the tumor.

Preferably, the surgery method according to the invention is fluorescence-guided; more preferably it is a method for the NIR fluorescence-guided surgery of a ROI in a patient which comprises using the fluorescent probe DA364 to generate the intraoperative detection of the tumor and a clear and precise demarcation of the borders of the tumor enabling its radical resection.

According to one preferred implementation, the step ii) and iii) of the guided-surgery method of the invention, that include generating the intraoperative imaging of the ROI and the detection of the margins of the tumor are conveniently carried out under fluorescent light, for instance as formerly discussed.

In practical terms, these steps can for instance be carried out by use of a surgical apparatus equipped with an excitation lamp and a suitable set of filters allowing to visualize the fluorescent probe accumulated in tumor and to identify thereof margins. To this extent, an excitation light is for instance used suitably filtered in the range from 600 to 700 nm and, preferably, in the range between 630 and 694. An emitted fluorescent light is thus obtained, which is suitably filtered in the range of from 650 to 1000 nm and, preferably, from 694 to 800 nm. When, instead, the fluorescence signal is not required, the surgical field can be properly illuminated with white-light, for instance by a cold light source. In this respect, suitable apparatus can conveniently be used, e.g. the FLARE system, which allows the detection of fluorescence leaving the surgical field with natural light, which, therefore, does not requires to turn on and off the fluorescence excitation light.

In one embodiment, the guided surgery method of the invention includes a step i) which comprises administering an effective amount of the DA364 fluorescent probe to the individual patient and then circulating it for an appropriate time.

In a preferred embodiment, the guided-surgery according to the invention is conveniently carried out in an individual patient pre-treated with an effective dose of the fluorescent agent DA364; in this respect the appropriate administration of the fluorescent agent to the individual patient is conveniently performed intravenously or intra-arterially, for instance within one week of the curative surgery, preferably within 48 hours, and, more preferably, in a time window of about 24 up to 48 hours before the guided curative tumor surgery.

A fluorescent imaging of the tumor area is thus generated under fluorescent light according to step ii) of the method of the invention, enabling a clear and unambiguous identification of the borders of the pathologic area undergoing curative surgical resection and helping the surgeon to identify the surgical margins of the pathological region to be resected, commonly including all the pathologic area up to the highly fluorescent tumor margins and an additional, likely healthy, extra region (or negative margin, as herein used interchangeably) around the tumor, for instance of at least 0.3 mm and, preferably, of about 0.5 mm up to about 1 cm and more than 1 cm, where the fluorescent signal is absent or consistent with the background (autofluorescence) signal generated by the normal, healthy tissue, compensating for any optional inaccurate determination of the tumor border.

A guided-surgery of the tumor region is then operated by the surgeon according to step iv) of the method of the invention, by following identified surgical margins of the tumor.

The fluorescent guided-surgery method of the invention can then optionally comprise an additional step v) which includes verifying the precision and the effectiveness of performed curative resection under fluorescent light and, optionally, repeating the surgery by following larger margins around detected tumor area, up to reach negative margins, namely margins around the excised tumor having none fluorescent signal.

In a particularly preferred embodiment, the invention relates to a method for the NIR fluorescence-guided surgery of a tumor of an individual patient, wherein the tumor is a prostatic tumor.

As formerly discussed, the fluorescent probe identified by the instant invention enables an improved and persistent demarcation of tumor margins under fluorescent light regardless of the kind of tumor or the reduced or non-homogeneous integrin expression it may display.

As such, it finds an advantageous use in a NIR fluorescent intraoperative detection of tumor margins and guided surgery protocol allowing to standardize the surgical resection of a tumor in an individual patient, that comprises using the compound DA364 and fluorescent light for the intraoperative or per-operative delimitation and demarcation of margins of the tumor undergoing curative surgery.

Accordingly, in a further embodiment the invention relates to a standardized protocol for the intraoperative imaging of tumor margins and the curative guided-surgery of a tumor in an individual patient which comprises:

a) administering of an effective amount of the DA364 fluorescent probe to the individual patient, for instance within one week, preferably at least 24 hours and, more preferably, in a time window of from 24 to 48 hours before the image-guided surgery;

b) exposing the body region of the individual patient comprising the tumor of interest to the surgeon visual inspection, e.g. by optional incision (of the concerned body region) and optional removal of interposed skin and tissue (s);

c) generating an intraoperative imaging of said individual patient body region, under fluorescent light, and detecting tumor margins;

d) operating the curative resection of the tumor by following detected margins, e) assessing the state of excised margins under fluorescent light and verifying the existence of negative margins around excised tumor or, alternatively, f) repeating the excision by following larger margins around tumor, and g) repeating steps e) and f) up to achieve negative (non-fluorescent) margins around excised tumor;

which constitutes an additional embodiment of the invention.

Each of the steps a)-e) of the protocol are carried out for example as previously discussed. To this extent, after performing the surgical removal of the tumor according to step d) of the protocol, the effectiveness of operated resection is verified under fluorescent light, according to step e) of the protocol, in order to assess the presence or the absence of negative margins, namely of a non-fluorescent, healthy, area around resected tumor. Then, if necessary, namely if fluorescent regions are still detected in the patient body area surrounding excised tumor or in the absence of negative margins around excised tumor, steps g) and h) of the protocol are repeated by following larger margins around tumor area, up to achieve negative tumor margins under fluorescent light. Non-fluorescent tissue surrounding excised tumor are then optionally collected and used for an additional pathological examination.

The potential of the solution provided by the present invention, namely the efficacy displayed by the DA364 in the intraoperative detection and demarcation of the margins of a tumor in an individual patient and, especially, in the radical resection of tumors, though having reduced or non-uniform integrin expression, has been assessed by means of in vitro and in vivo tests.

To this extent, the fluorescent characteristics of DA 364 probe were first assessed, and then the affinity displayed by DA364 toward integrins was measured (examples 2-4).

An association constant ($k_a$ ($M^{-1}$)) with HSA of 2.8670 $10^4 \pm 0.1140 \cdot 10^4$ for DA364 was also determined (Example 5) and the plasma kinetic (Example 6).

The reliability of the visual estimates of the tumor margins obtained under fluorescent light with the NIR agent identified by the present invention during the intraoperative inspection and guided resection of a tumor, and its surgical efficacy have been then verified with in vivo tests carried out on rats model having orthotopic Mat-Ly-Lu prostate tumor.

To this extent, the prostate cancer, which does not belong to tumors having high $\alpha_v\beta_3$ expression, was purposely chosen to demonstrate the unexpected ability shown by DA364 to provide, in addition to optimal targeting and accumulation properties in tumors having a high $\alpha_v\beta_3$ integrins expression, a preferential accumulation also in tumors having a reduced or non-uniform expression of these receptors, which is fully adequate to enable an effective support to the surgeon in the intraoperative inspection of a tumor region and guided surgery of the tumor. In fact, it is known in the relevant art that both the species of integrins expressed in prostatic cancers, and their concentration, are parameters far from being recognized with certainty. Indeed, the expression of $\alpha_v\beta_3$ integrins in prostatic cancers still remain a rather indefinite value, ranging from strong to none and known to be dependent on individual patients (The Prostate 70:1189-1195 (2010), where this likely is the reason because the targeting of prostate cancer and its detection is at now commonly obtained by exploiting the active sites of the Prostate Specific Membrane Antigen (PMSA), a membrane bound glycoprotein that is overexpressed almost exclusively by prostate epithelium of malignant prostate cells and their metastases (see, for instance J. Med. Chem. 2009, 52(2) 544-550 and Trans. Androl. Urol. 2013; 2 (3):254-264 and cited literature).

In this context, it should be noted that the relevant literature on animal tumor models (see for instance Ann Nucl Med 2011 Dec. 31; 25(10):717-31) excludes in fact RGD-based targeting tracers from appropriate targeting tracers for MAT-Ly-Lu prostatic tumor.

As illustrated in detail in the working examples, it has now been surprisingly assessed the efficacy of DA364 in the surgical treatment of the above cited rat orthotopic MAT-Ly-Lu prostatic tumor model, which may be classified as a tumor having reduced expression of $\alpha_v\beta_3$ integrins. Further of demonstrating the ability of DA364 of been used in intraoperative fluorescence-guided surgery for low-integrin overexpression tumors, this result supports the choice of the prostatic tumor as an appropriate model representative of a tumor having reduced or non-homogeneous expression of $\alpha_v\beta_3$ integrin receptors.

Furthermore, as illustrated in the in-vivo working examples, DA364 is suitable for the intra- or pre-operative visualization of a region of interest comprising other tumors with reduced over-expression of $\alpha_v\beta_3$ integrin receptors. Representative of these low $\alpha_v\beta_3$ integrin expressing tumors (in addition to the above cited rat orthotopic MAT-Ly-Lu prostatic tumor model) is A431 tumor model (a xenograft mouse model of human epidermoid carcinoma reported to have low expression of integrins), as illustrated in the working examples, as well as human ovarian or colorectal adenocarcinoma.

These results are very promising, especially because in the experimental test of Example 7 the excision of the tumor region has been performed strictly following the tumor margins identified under fluorescent light and demarcated by a high intensity fluorescence signal, without including a larger volume around detected tumor margins, for instance of at about 0.5 mm of healthy (low fluorescent) tissue, as recommended for a safer surgical strategy.

These results also confirm the large operational time-window (from 4 to more than 24 hours) provided by the compound identified by the present invention, as the imaging agent allows a clear demarcation of the prostatic tumor still 24 hours after injection of a minimum amount of the contrast agent, while the circulating agent is hardly observable after 4 hours from intravenous administration.)

Furthermore, the experimental images show that the administered agent is detectable both inside the tumor cells and in the surrounding interstitial space.

All these results are consistent with and confirm the potential unexpectedly shown by the fluorescent probe identified by the present invention to offer a reliable real-time feedback to the surgeon, by promoting a sharp and persistent demarcation of tumor margins under fluorescent light allowing to operate curative resections of tumors with proved good efficacy, even in the presence of tumors having a reduced or suboptimal or non-uniform expression of $\alpha_v\beta_3$ integrins that represent the natural target of the DA364 probe.

Further details concerning the fluorescent agent DA364 and its use according to the present invention are reported in the following experimental section, with the sole aim to better illustrate the present invention, without representing any limitation to it.

EXPERIMENTAL PART

Figure 1:
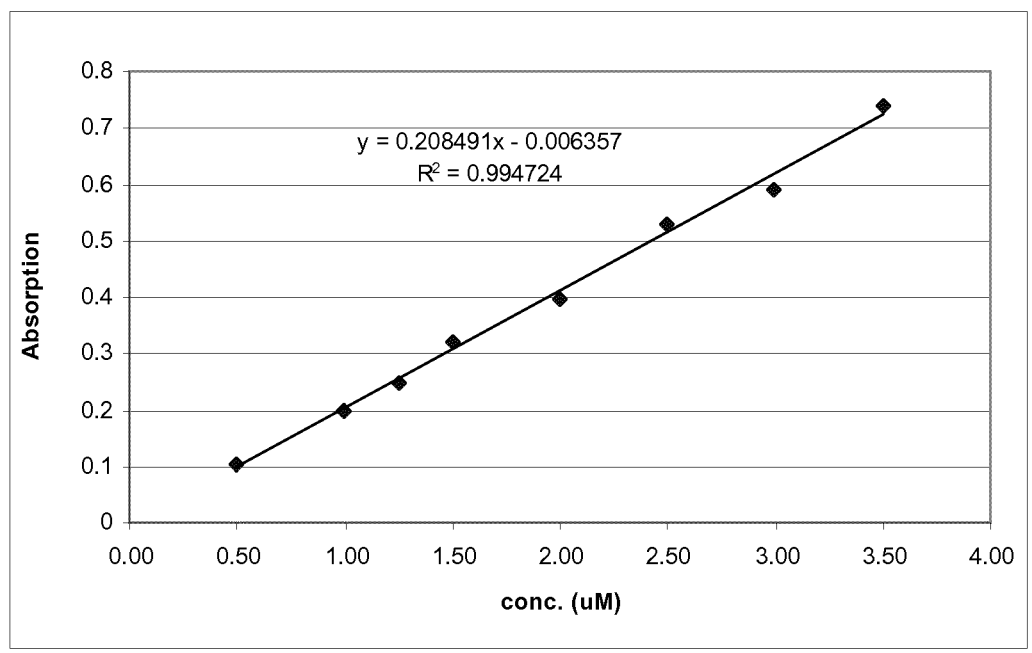
FIG. 1. Linear regression for the evaluation of the molar extinction coefficient of the fluorescent probe DA364.

Example 1 Preparation of the NIR Agent DA364

The preparation of the NIR agent DA364 was performed substantially as described in the formerly quoted reference *Contrast Media Mol. Imaging* 2011, 6, 449-458, by using the synthetic procedure schematized above

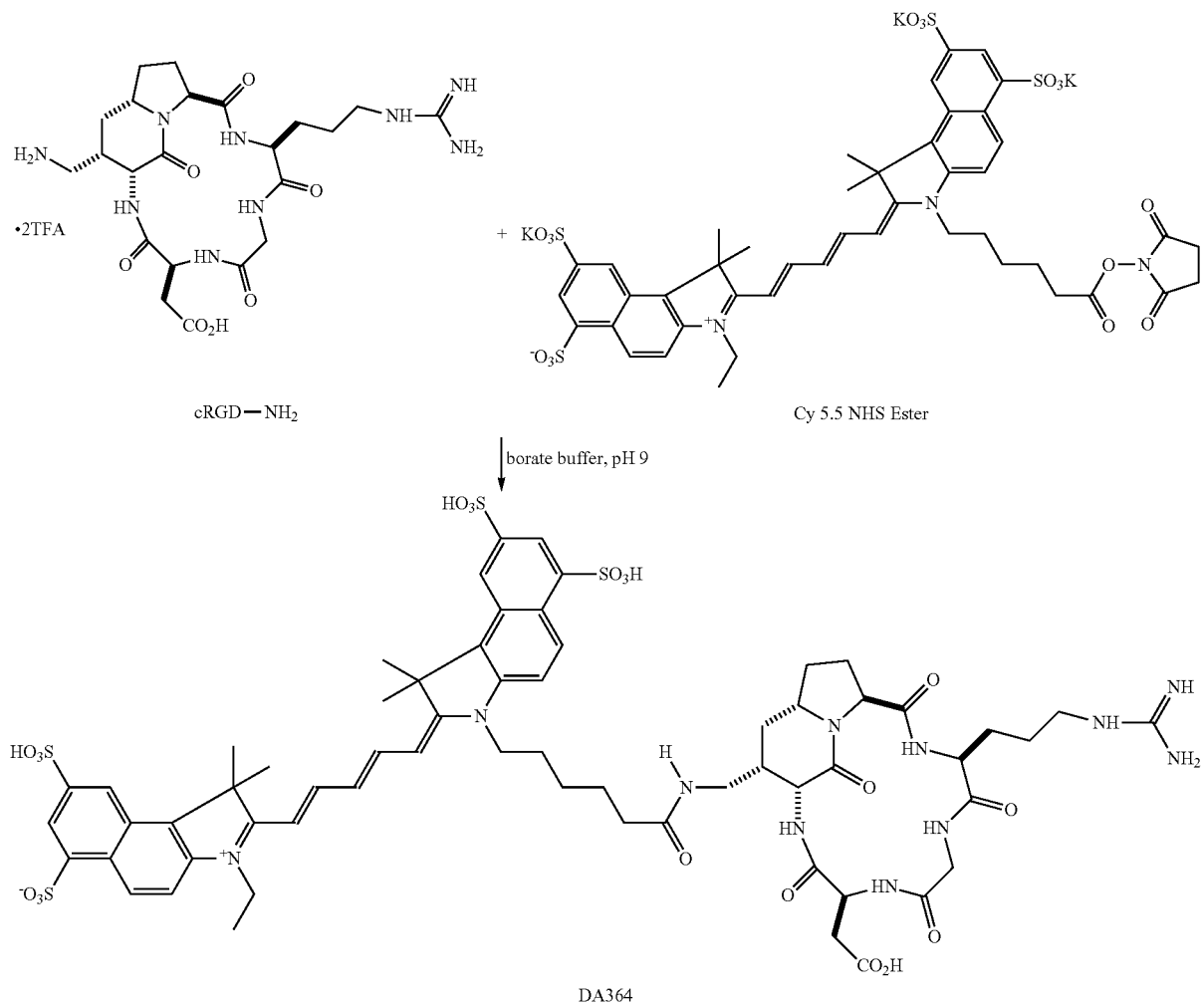

DA364 including:

1) Preparation of the Integrin Targeted Cyclic Pentapeptide cRGD-NH$_2$

The preparation of the integrin targeted peptidomimetic moiety cRGD-NH$_2$ was carried out substantially as described in WO2006/095234 and, in better details, respectively in *Angew. Chem. Int. Ed.,* 2010, 49, 7111-7115, *J. Org. Chem.* 2005, 70, 4124-4132 and *Chem Med. Chem.* 2009, 4, 615-632 describing, respectively, the preparations of the individual intermediates and the cyclic cRGD-NH$_2$ integrin targeted scaffold according to the following schemes:

a. Synthesis of Intermediate 5

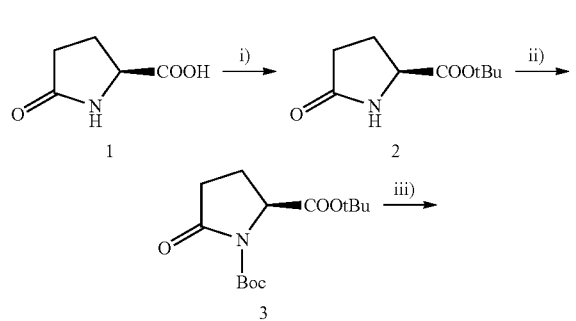

b. Synthesis of Intermediate 10

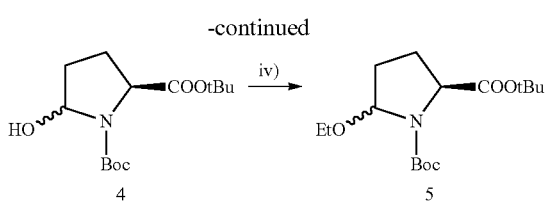

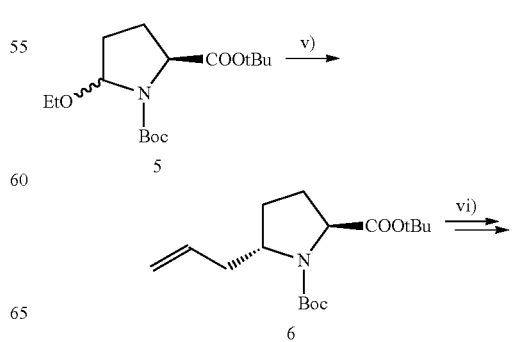

-continued
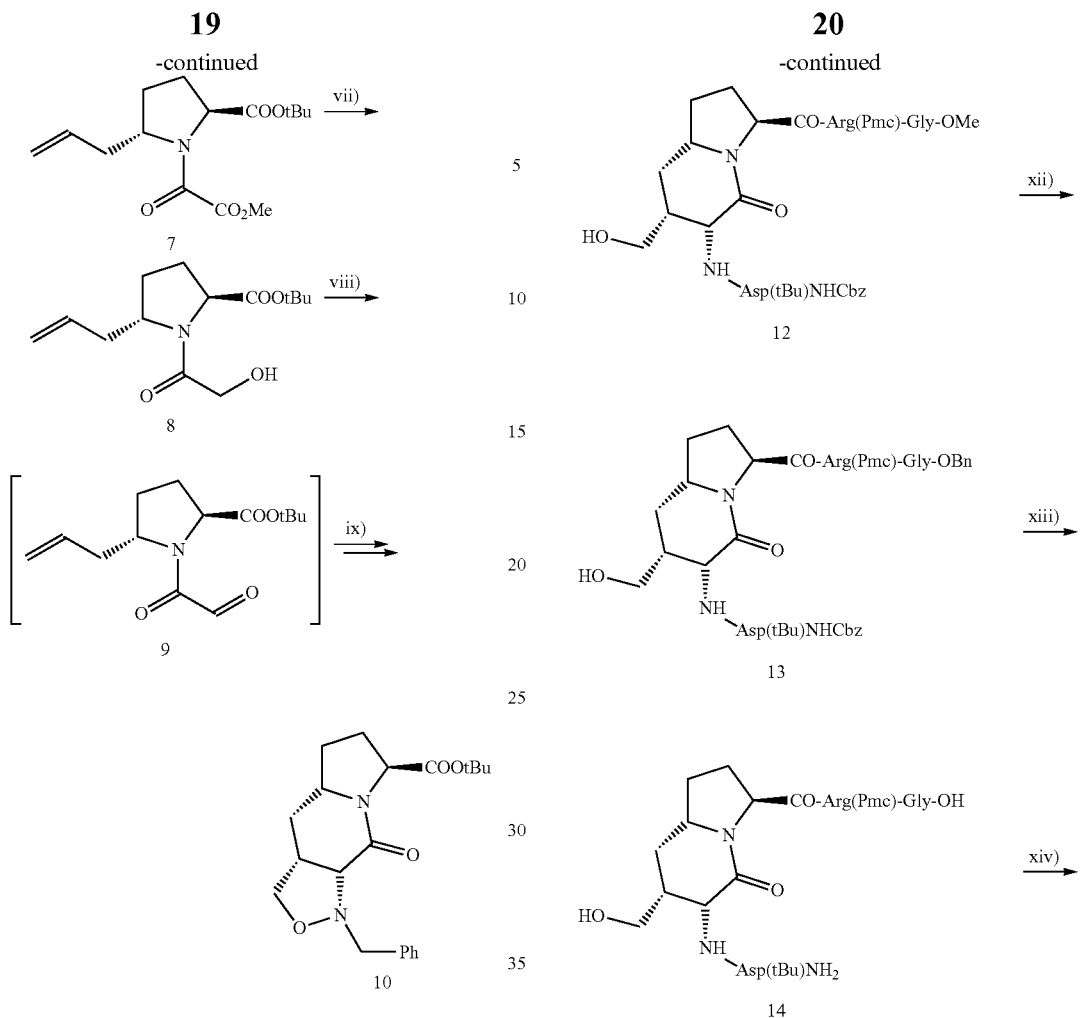
c. Synthesis of cRGD-NH₂
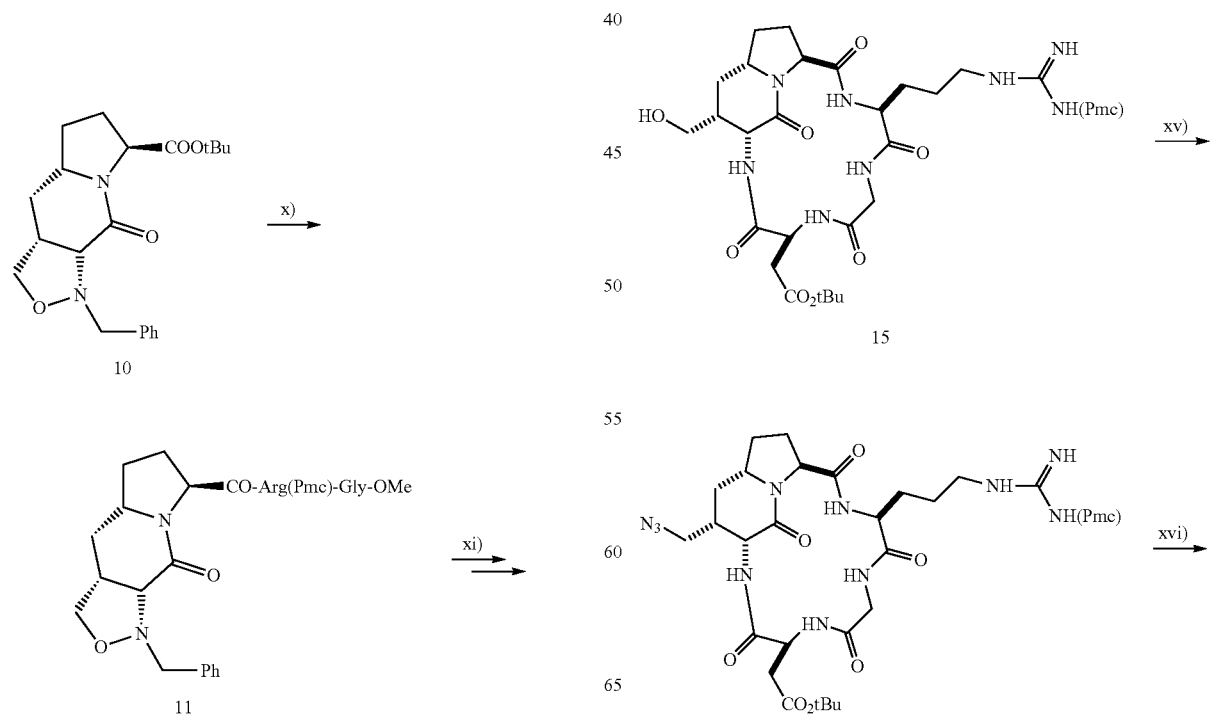

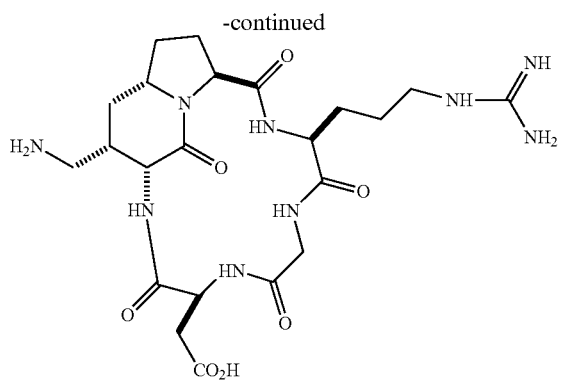

2) Preparation of the NIR Agent DA364

A solution of Cy5.5-NHS ester (13 mg, 0.011 mmol) (purchased from GE Healthcare, Product Code PA15602) in borate buffer pH 9 (4 mL) was added with a solution of cyclic cRGD-$NH_2$ scaffold (8.8 mg, 0.011 mmol) in borate buffer pH 9 (3.5 mL). The reaction mixture was stirred for 24 h at room temperature and protected from light (resulting pH 8.1). At the end of the reaction (assessed by HPLC-MS) the crude reaction is diluted with a 5% CH3COOH aqueous solution (1.5 mL) and the residual reaction solvent was then removed by freeze-drying.

The crude product was purified by preparative HPLC (eluent A: $H_2O$+0.1% TFA, eluent B: $CH_3CN$+0.1 TFA, flow: 15 mL/min, stationary phase: Waters Atlantis Prep T3 OBD 5 μm, 19×100 mm, detection: UV, $\lambda_1$: 210 nm, $\lambda_2$: 254 nm) to give the desired product as a dark blue solid (11.8 mg, 0.0082 mmol) after freeze-drying. Yield: 74.6%. HPLC purity: 92.96% (as area %)

Analytical Characterization

Analytical characterization of the obtained NIR Agent was performed by HPLC-MS and $^1$H-NMR.

Nuclear Magnetic Resonance $^1$H-NMR spectra was recorded at 298 K in DMSO-d6 or $D_2O$, with a Bruker Avance-III ($^1$H, 600.13 MHz) with deuterium as lock channel.

Recorded $^1$H-NMR was consistent with the expected structure.

HPLC-UV-MS Preparative Method

LC column: Agilent Zorbax SB-PHENYL—250 mm×4.6 mm×5 μm (P/N:880975-312)

HPLC parameters

Instrument: Triple quadrupole Thermo Fisher LC Accela equipped with Accela Pump, Accela Autosampler, Accela PDA Detector and TSQ Quantum Access.

Injection volume: 5 μl (with a sample concentration of 200 μg/ml)

Column oven: 40° C.

Tray temperature: 5° C.

Wash needle program: inside needle washing occurs to prevent memory effects.

Washing solution: 40:50:10—water:methanol:i-propanol

Uv-vis acquisition range: 200-790 nm (Tungsten lamp needing:max abs. 776 nm)

MSD acquisition range: 50-1500 a.m.u.

MSD mode: ESI both polarities (positive and negative, negative is preferred)

The compound under analysis was diluted with milli-Q water.

Pump flow:0.5 ml/min; Max pressure: 400 bar

Solvent A:Water+ammonium acetate (1 g/l); Solvent B:Acetonitrile 100%

Stop time: 42 mins.

Gradient:

| Time (min) | A (%) | B (%) |
|---|---|---|
| 0 | 98 | 2 |
| 2 | 98 | 2 |
| 10 | 80 | 20 |
| 25 | 70 | 30 |
| 30 | 64 | 40 |
| 35 | 0 | 100 |
| 36 | 98 | 2 |
| 42 | 98 | 2 |

Fluorimetric Characterization of DA364

Example 2: Determination of the Extinction Coefficient

Material and Methods

A dual-beam Perkin Elmer Lambda 40 UV-VIS spectrophotometer was used to determine the extinction molar coefficient of the NIR agent DA364.

Two standard stock solutions containing the NIR agent in PBS at 1000 μM (sol I: 1.27 mg, 0.884 mL) and 1250 μM (sol II: 7.03 mg, 3.915 mL) were prepared. Diluted standard solutions were then prepared as reported in Table A by diluting the stock solutions in an appropriate volumetric flask using PBS. The absorbance of each standard diluted solution was measured without any further dilution.

TABLE A

Standard solutions dilution table

| Standard | Concentration, μM | Stock Sol. I, mL | Stock Sol. II, mL | V tot, mL |
|---|---|---|---|---|
| Blank | 0 | 0 | 0 | — |
| STD 1 | 1.25 | | 0.050 | 50 |
| STD 2 | 2 | | 0.040 | 25 |
| STD 3 | 3 | | 0.060 | 25 |
| STD 4 | 1 | | 0.040 | 50 |
| STD 5 | 0.5 | 0.050 | | 100 |
| STD 6 | 1.5 | 0.030 | | 20 |
| STD 7 | 2.5 | 0.050 | | 20 |
| STD 8 | 3.5 | 0.035 | | 10 |

Results

The absorbance of each diluted standard solutions was measured and the molar extinction coefficient of DA364 was calculated from the slope of the linear regression reported in FIG. 1. The measured extinction coefficient in this condition was 208500 $M^{-1} \cdot cm^{-1}$ (corresponding to 83% of the theoretical value reported for Cy5.5 dye: 250000 $M^{-1} \cdot cm^{-1}$).

Statistical analysis was also carried out (data not reported) to verify the linear regression reliability.

Example 3: Assessment of the Fluorescence Quantum Yield

Material and Methods

Fluorescence quantum yields (0%) measurements were performed on FluoroLog-31IHR-320 (HORIBA-JobinYvon) with integrating sphere accessory.

The measurements were carried out using an excitation wavelength of 625 nm and using a 450W Xenon Light Source. Detection was performed on TBX-04 detector from 645 to 850 nm (excitation and emission slit were 1.8 nm).

The fluorescence quantum yield of DA364 solution was measured both in human serum SERONORM (human-based control serum), NycomedPhama, batch 1109514) and in Phosphate Buffer Saline (PBS).

Solutions of the NIR agent were prepared in PBS and in human serum with absorbance lower than 0.1. Fluorescence (Φ%) measurements were carried out after incubation of the NIR agent at Room Temperature (RT) for 15 min.

Results

Obtained Φ% values, reported in Table B below, show that DA364 exhibits a quantum yield of 36.5% (±2.37) in PBS and 57.5% (±1.26) in SERONORM (human-based control serum).

Figure 2:
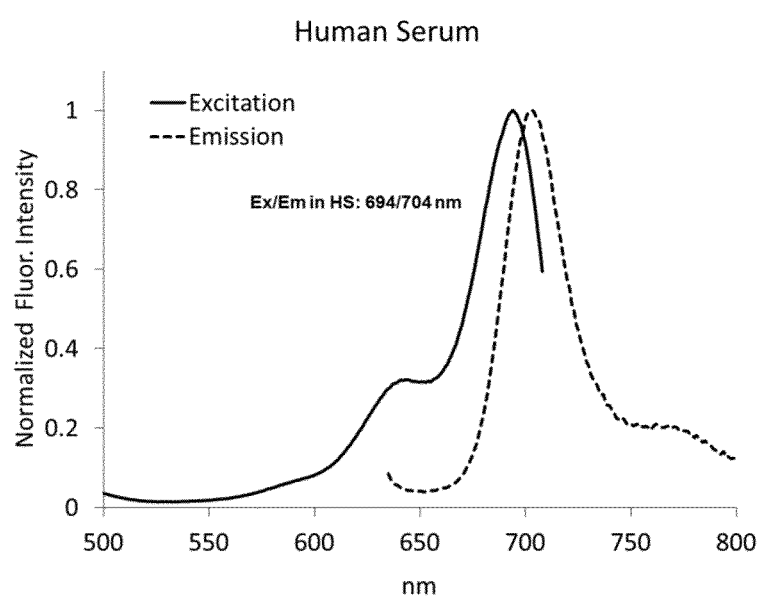
FIG. 2 shows excitation and emission spectra of DA364 in PBS (left plot; ex/em: 674/694; SS:20 nm) and in SERONORM (human-based control serum) (right plot; 694/704, SS:10 nm).

The normalized excitation and emission spectra of the NIR agent in PBS (ex/em: 674/694; Stokes Shift: 20 nm) and in SERONORM (human-based control serum) (694/704, Stokes Shift 10 nm) are shown in FIG. 2. As shown in the figure, the interaction of the DA364 contrast agent with serum albumin promotes the shift of the emission maximum from 694 nm to 704 nm (in PBS and in SERONORM (human-based control serum) respectively) and also the reduction of the Stokes shift.

TABLE B

Φ% values for DA364 in PBS and SERONORM (human-based control serum)

|  | PBS | SERONORM (human-based control serum) |
|---|---|---|
| Φ% | 36.5 (SD 2.37) | 57.5 (SD 1.26) |

Biological Characterization of DA364

Example 4: In Vitro Competitive Binding Assay Towards $\alpha_v\beta_3$, $\alpha_v\beta_5$ and $\alpha_v\beta_1$ Integrins The affinity of DA364 for its specific targeted (the integrin $\alpha_v\beta_3$) and its crossreactivity for other integrins (e.g. $\alpha_v\beta_1$, $\alpha_v\beta_5$) was assessed by in vitro binding tests.

Material and Methods

A 96-well microtiter plate (MediSorp, Nunc) was coated overnight at 4° C., with tested integrins (0.5 µg/mL, diluted in coating/washing buffer (20 mM Tris HCl pH 7.4; 150 mM NaCl; 1 mM MnCl2; 0.5 mM MgCl2; 2 mM CaCl2). After coating, the plate is rinsed with washing buffer and then incubated in blocking buffer (3% BSA in coating buffer) for 2 h at room temperature (RT) (24° C. in Thermomixer, under shaking). The plate was then rinsed in washing buffer and incubated at RT for 3 h with DA364 (concentration range from 5000 to 0.005 nM). DA364 solutions were prepared by serially diluting a stock solution of the NIR agent in 1% BSA in coating buffer in presence of biotinylated vitronectin (1 µg/mL, cod. HVN-U605, Molecular Innovations). The plate is then rinsed again and incubated with Streptavidin-HRP (cod.EG RPN 1051, GE Healthcare) (1:10000 in PBS) 1 h at RT, binding the biotinylated vitronectin. After additional washes in PBS, the plate was incubated with TMB solution (3,3',5,5'-tetramethylbenzidine) (cod.T-0440, Sigma-Aldrich) for 5-10 min and the colorimetric reaction was then stopped by addition of 2 N sulfuric acid. The quantification of the IC50 for DA364 was performed by measuring the competitor (biotinylated vitronectin) by reading the absorbance at 450 nm. IC50 values were determined by least-square non-linear regression analysis.

Results

The competitive binding assays with vitronectin, the natural substrate of $\alpha_v\beta_3$, demonstrated the high affinity of DA364 for its specific target, namely the $\alpha_v\beta_3$, and lower affinity for the analogue $\alpha_v\beta_5$; a crossreactivity is moreover highlighted for $\alpha_v\beta_1$.

Obtained affinity results for integrins $\alpha_v\beta_3$, $\alpha_v\beta_5$ and $\alpha_v\beta_1$ are provided in Table C below.

TABLE C

Binding affinities of DA364 to integrins expressed as vitronectine IC50

|  | IC50 (nM) | SE |
|---|---|---|
| $\alpha_v\beta_3$* | 3.76 | 0.65 |
| $\alpha_v\beta_5$ | 280.57 | 0.97 |
| $\alpha_v\beta_1$ | 28.03 | 1.22 |

*Average value from a triplicate test

Example 5: In Vitro Binding Assay Towards Human Serum Albumin (HSA)

The affinity of DA364 for the HSA was determined by the spectroscopic measurements of the absorbance, according to the procedure disclosed in, for instance, Connors, K. A. (1987) Binding Constants. The Measurement of Molecular Complex Stability, John Wiley & Sons, New York (see, in particular, chapter 4).

Material and Methods

A dual-beam Perkin Elmer Lambda 40 UV-VIS spectrophotometer was used to acquire absorption spectra of DA364 incubated with HSA. Two standard solutions containing HSA were prepared fresh daily in PBS at 75 mM and 500 mM and kept under stirring for about 30 min and 1 h respectively.

A stock solution of DA364 (845±5 mM) was diluted 1:20 and mixed with HSA (HSA Sigma Aldrich, batch 049K7535, item A1653) to give a ramp of concentrations (0, 1, 10, 20, 40, 60, 30, 80, 100, 200, 400 mM). Final solutions, containing 0.99 mM of the NIR agent and different amount of HSA, were incubated 1 h at room temperature before measurements. The absorbance of each solution was measured against a reference solution of HSA at the same concentration. The absorbance values measured at the wavelength of 689 nm (corresponding to the maximum absorption of DA364 bound to HSA) were fitted using the following equation:

$$\frac{\Delta A}{b} = \frac{\Delta\varepsilon \cdot k_a [HSA] C_{DA364}}{k_a [HSA] + 1}$$

where $\Delta\varepsilon$ is the difference of molar absorptivities obtained from free and bound DA364, $\Delta A$ is the difference in the absorbance of DA364 and reference solutions, b is the length of the optical path through the solutions, [HSA] is the concentration of HSA, $C_{DA364}$ is the concentration of the fluorophore and $k_a$ is the association constant.

Results

The association constant with HSA ($k_a(M^{-1})$) measured for DA364 was $2.8670 \cdot 10^4 \pm 0.1140 \cdot 10^4$ ($R^2 = 0.9949$).

This result demonstrates the existence of an affinity towards serum albumin displayed by the NIR agent identified by the present invention, which is consistent with the in vivo hybrid behaviour it displays, allowing its accumulation and diffusion towards tumors as a results of both an high specificity for integrins receptors and an non-specific retention, e.g. mediated by a non-specific binding to extracellular components, including extravascular (leaked) albumin.

Example 6: Assessment of the Plasma Kinetic of DA364

The plasma kinetic of the NIRF probe DA364 was evaluated after a single intravenous administration in CD-1 (ICR)BR mice.

Protocol

The fluorescent probe is administered at dose of 0.4 µmol/kg, corresponding to about 10 times the effective dose used in imaging studies (1 nmol/mouse, considering an average mouse body weight of 25 g). Animals were sacrificed at different time points up to and including 14 days after treatment and blood samples were collected for the determination of DA364 content, performed by using an HPLC method coupled with a fluorimetric detector.

Preparation of the Formulation

DA364 was supplied as a 655 µM bluish solution. Some days before the animal administration, after being thawed, the 655 µM solution of DA364 was diluted up to the final concentration of 0.04 µmol/mL. To this end, 0.8 mL of the 655 µM solution of DA364 was diluted with 12.2 mL of 0.9% NaCl physiological saline. The 0.04 µmol/mL formulation was stored at −80° C. until administration.

Animals

The experiment was performed with CD-1(ICR)BR mice (40 males; weight at arrival: 22-30 g; age: 4-5 weeks old), purchased from Charles River Laboratories Italia, Calco (LC), Italy. All procedures involving the animals have been conducted according to national and international laws and policies for the Care and Use of Laboratory Animals (L.D. 116/92; Authorization n.19/2008-A issued Mar. 6, 2008, by the Italian Ministry of Health; EEC Council Directive 86/609CEE, and EEC Council Directive 2010/63/EU).

Experimental Design

The plasma kinetic of DA364 was measured in a pharmacokinetic study. A period of at least 3 days was allowed between animal arrival and treatment. On the day of dosing, animals were randomly assigned to the pharmacokinetic time points and to the calibration group. Animals were identified by colored marks made on the tail. Each cage label was uniquely numbered with study number, compound, administration route, species, dose, date of treatment and date of sacrifice and animal numbers.

The NIR agent DA364, pre-warmed at room temperature, was intravenously injected at a dose of 0.4 µmol/kg, via tail vein, at an injection rate of 1 mL/min with a Harvard infusion pump. The administered dose corresponds to about 10 times the effective dose used in imaging studies. The intravenous administration route was chosen as possible route of exposure for humans.

Experimental Scheme:

Animals (three for each time point) were sacrificed before and 5 min, 10 min, 20 min, 30 min, 60 min, 4 h, 24 h, 48 h, 7 days and 14 days after DA364.

Seven animals were moreover used, to collect blank plasma for the calibration curve.

The day of sacrifice animals were anesthetized with sevoflurane, at an expiratory concentration of 3-4% in induction and 2-3% in maintenance and then sacrificed by decapitation. Blood for HPLC determinations (at least 0.5 mL) was collected using heparinized tubes. Plasma obtained after centrifugation (2100 g for 10 min) was stored at −80° C. until the day of analysis.

Assessment of DA364 in Plasma

Determination of the amount of DA364 in plasma samples was carried out by an HPLC method coupled with a fluorimetric detector previously prompted.

Preparation of the Acetate Buffered Solution of DA364

Acetate buffer solution was prepared by dissolving 1 g of Acetate buffer in 1 L of Milli-Q water. The appropriate amount of the NIR agent was then added to the obtained solution.

Preparation of Plasma "CAL" Samples

Calibration standards (CAL) were prepared by adding 10 µL of DA364 acetate buffer solution (from 0.04 to 4 nmol/mL), and 100 µL of a Methanol and Acetonitrile solution (50:50) to 90 µL of blank plasma. Tubes were stirred and subsequently centrifuged at 4° C. for 10 minutes at 13000 g. Ten microliters of the clear supernatant were injected into the HPLC equipment.

Preparation of Plasma "QC" Samples

Quality controls (QC) were prepared by adding 10 µL of DA364 acetate buffer solution (from 0.06 to 3 nmol/mL), and 100 µL of a Methanol and Acetonitrile solution (50:50) to 90 µL of plasma. Tubes were stirred and subsequently centrifuged at 4° C. for 10 minutes at 13000 g. Ten microliters of the clear supernatant were injected into the HPLC equipment.

Preparation of Plasma "S" Samples

Plasma samples (S) were prepared by adding 100 µL of acetate buffer and 100 µL of a Methanol Acetonitrile solution (50:50) to 100 µL of diluted plasma. Tubes will be stirred and subsequently centrifuged at 4° C. for 10 minutes at 13000 g. Ten microliters of the clear supernatant will be injected into the HPLC equipment. Appropriate dilution was performed in case of plasma samples too concentrated.

Chromatographic Conditions

Chromatographic: Waters Alliance 2695XC

HPLC column: Zorbax SB-Phenyl, 5 µm, 250×4.6 mm

Mobile phase A: Dissolve 1 g of Acetate buffer in 1 L of Milli-Q water (0.013 M, pH −7.0)

Mobile phase B: Dissolve 1 g of Acetate buffer in 1 L of Methanol and Acetonitrile (50:50)

Sample Temperature: 10° C.

Column Temperature: 60° C.

Injection volume: 10 µL

Detector: FL detector Waters 2475; excitation wavelength: 670 nm; emission wavelength: 700 nm Run time: 23 min Elution: gradient

| Time (min) | % A | % B | Flow |
| --- | --- | --- | --- |
| 0 | 91 | 9 | 1.0 |
| 5 | 91 | 9 | 1.0 |
| 11 | 44 | 56 | 1.1 |
| 15 | 44 | 56 | 1.1 |
| 17 | 91 | 9 | 1.0 |
| 23 | 91 | 9 | 1.0 |

The HPLC determination was performed by interpolating calibration curves of DA364 in plasma and organs, prepared by assaying calibration standard samples (CAL) (6 concentrations, 3 replicates for each concentration) of the fluorescent agent DA364.

Data Analysis

Blood for HPLC determinations (at least 0.5 mL) was collected in heparinized tubes. Plasma concentration of DA364 was measured by an HPLC method coupled with a fluorimetric detector.

To evaluate the systemic exposure, $C_{max}$ and the area under the plasma DA364 concentration curve as a function of time (AUC) were calculated by non-parametric methods using the computer program WIN-NONLIN 6.3 (WinNonlin 6.3 SCI Software, Lexington, Ky., USA). For the tested dose, a non-compartmental analysis was performed using the average plasma concentrations from 3 animals for each time point. For $C_{max}$ and the corresponding $t_{max}$ the observed values were reported. Area under the plasma concentration-time curve to the last observable plasma concentration ($AUC_{(0\ to\ t)}$) was calculated from observed data using the logarithmic trapezoidal method. In realta possiamo dire di calcolare anche $t_{1/2}$, Vd, e Cl.

Da 364 content in organs will be reported as μg/mL (blood) or μg/g of tissue. Data will be transformed to percent of injected dose (% ID) in each organ. Mean and standard deviation will be then calculated for each sampling time.

Results

Figure 6:
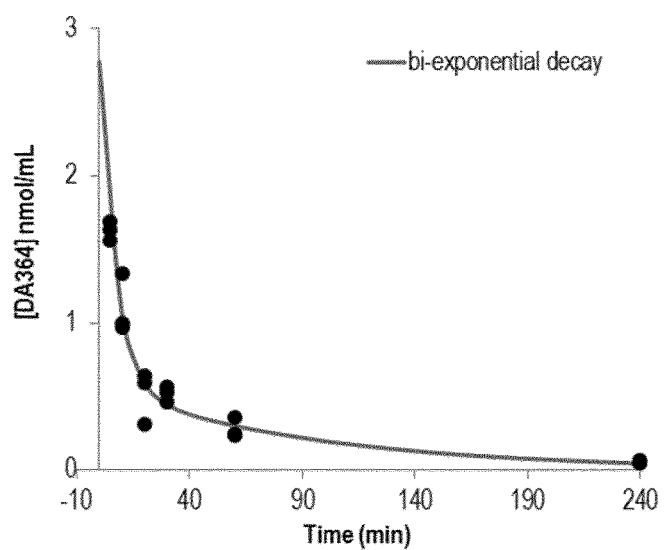
FIG. 6 shows the DA364 plasma concentration (concentration of free agent in circulating blood) time curve recorded in the Experimental test of Example 6. The fast elimination of the circulating DA364 probe from the plasma compartment is clearly shown in the plot.

Plasma concentration of DA364, measured by fluorescence after HPLC separation are included in the Table D below and, graphically, in FIG. 6. Obtained results confirm the rapid clearance of the free, circulating agent, reaching a negligible concentration in the blood 4 hours after the administration to test animals, which becomes then less than the instrumental detection limits (LOD=0.0012 nmol/mL).

TABLE D

| Time (min) | nmol/mL (Mean from a triplicate result) | s.d. |
|---|---|---|
| 5 | 1.629 | 0.063 |
| 10 | 1.10 | 0.20 |
| 20 | 0.612 | 0.035 |
| 30 | 0.518 | 0.052 |
| 60 | 0.278 | 0.066 |
| 240 | 0.051 | 0.013 |
| 1440 | <LOD | <LOD |
| 2880 | <LOD | <LOD |
| 10080 | <LOD | <LOD |
| 20160 | <LOD | <LOD |

$C_{max}$ of 1.629 nmol/mL was measured at 5 minutes ($t_{max}$) after injection. The half life values associated with the terminal elimination phase was 64 min. The $AUC_{(0\ to\ \infty)}$ value was 77 min*nmol/mL. The total plasma clearance value was 5 mL/min/kg (0.15 mL/min). The clearance value results well lower than mice hepatic and renal blood flow (1.8 and 1.3 mL/min) suggesting accumulation in body (o other tissue). The volume distribution value at a steady state ($V_{dss}$) was 329 mL/kg (10 mL), slight lower than mice total body water (14.5 mL), suggesting extravasation of DA364 from the plasma compartment.

Example 7: Fluorescence Guided-Surgery in a Rat Prostate Tumor Model Using DA364 as NIR Fluorescent Probe This example is aimed at assessing the sensitivity of the NIR RGD cyclic probe DA364 in the recognition of tumor masses using rat orthotopic prostate tumor model Mat Ly-Lu (a tumor with reduced expression of $\alpha_v\beta_3$ integrins, as illustrated below).

Intraoperative imaging was performed on a Zeiss system, a modified surgical microscope including appropriate filters for illumination and selection of signals emitted from the probe. Rat tumoral MatLyLu prostate cells were inoculated in the right ventral lobe of the prostate. Three-four days after inoculation animals were intravenously injected with a dose ranging from 5 to 20 nmol/rat of NIR fluorescent probe and imaged 24 hours after. Tumors have been then resected through fluorescent signal guide. Tissues surrounding the fluorescent area including tissues from the left prostate lobe was excised for histological comparison. All the samples were analysed through routine histological processing (Hematoxylin and eosin stain) and additional immune-labelling.

Tumor Cells and their Preparation

Prostatic tumor Mat-Ly-Lu cell line, a subline of the rat prostatic adenocarcinoma model G-Dunning R-3327, was supplied by European Collection of Cell Culture (ECACC). Cells were grown in RPMI 1640 medium supplemented with 10% Foetal Bovine Serum (FBS), 2 mM glutamine, 100 IU/mL penicillin, 100 μg/mL streptomycin and 250 nM dexamethasone (DXMT). The trypan-blue exclusion test was used to assess cell viability before cells inoculation. Viability was expressed in % (ratio of viable cells to total cells×100). Cell cultures with a viability <70% were discarded. Human prostatic adenocarcinoma PC-3 cell line was supplied by American Type Culture Collection (ATCC). Cells were grown in Ham's F-12 medium supplemented with 10% Foetal Bovine Serum (FBS), 2 mM glutamine, 100 IU/mL penicillin, 100 μg/mL streptomycin. The trypan-blue exclusion test was used to assess cell viability before cells inoculation. Viability was expressed in % (ratio of viable cells to total cells×100). Cell cultures with a viability <70% were discarded. Human melanoma cell line WM-266 was supplied by American Type Culture Collection (ATCC). Cells were grown in Eagle's Minimum Essential Medium supplemented with 10% Foetal Bovine Serum (FBS), 2 mM glutamine, 100 IU/mL penicillin, 100 μg/mL streptomycin.

$\alpha_v\beta_3$ Expression

The expression of $\alpha_v\beta_3$ integrin in MatLyLu cell line was measured by western blot by comparison with WM266 melanoma cell line, known to have a high integrin overexpression (Anticancer Research 33:871-880 (2013)). In order to extract total proteins, cells pellets were dissolved in Lysis buffer (Tris-HCl pH 8 50 mM, NaCl 150 mM, EDTA 1 mM, NaF 100 mM, glycerol 10%, MgCl2 1 mM, TritonX-100 1%, Protease Inhibitors), subjected to 3 rounds of freeze and thaw (−80° C./37° C.) and left in ice for 20 min. Obtained solution was then sonicated for 10 s and centrifuged at 14000 g at 4° C. for 15 min. The protein content of the supernatant was then quantified with BCA method. To this extent, total extract was loaded in a 10% polyacrylamide gel and electrophoresis was applied to separate the proteins based on their molecular weight in denaturing conditions (20% SDS). Proteins within gel were then transferred onto a nitrocellulose membrane and subsequently blotted with the antibodies anti-$\beta_3$ integrin. Specific signal was visualized as a single or multiple band by chemiluminescent detection method. The images of labelled nitrocellulose were acquired by the ChemiDoc MP Imaging system and the area of the band relative to $\beta_3$ expression level was quantified with the software Image Lab v.4.1.

The expression of $\alpha_v\beta_3$ in MatLyLu cells was also measured by Flow cytometry (FACS) method and compared to the expression of the PC3 cell line.

To this extent, cells were recovered and washed in PBS supplemented with 0.2% BSA and 0.01% sodium azide. Nonspecific sites were blocked with rabbit IgG (Sigma-Aldrich). Cells were then incubated with the anti-$\alpha_v\beta_3$ integrin antiboby (dilution 1:100; clone LM609, Millipore) or an isotype-matched negative control for 30 min at 4° C., and subsequently incubated with fluorescein isothiocyanate (FITC)-conjugated rabbit anti-mouse Ig (DakoCytomation). Samples were collected and analyzed with a CyAn ADP flow cytometer and the Summit 4.3 software (DakoCytomation). Cells were gathered according to their light-scattering properties to exclude cell debris, and according to their propidium iodide (Sigma-Aldrich) negativity to exclude dead cells.

Figure 8:
FIG. 8 Flow cytometry of $\alpha_v\beta_3$ integrin expression in rat prostatic tumor Mat-Ly-Lu cells and in human prostatic tumor PC3 cells, used as internal reference. Expression of $\alpha_v\beta_3$ integrin is shown in the gray histograms, and the background of mouse IgG negative control is shown by the marker. Numbers show percentage of positive cells, calculated by subtracting the value obtained with isotype-matched control Ig from that detected with the specific mAb.

Western blot analysis resulted in a negligible expression of $\alpha_v\beta_3$ integrin by MatLyLu cells as compared to the expression by WM266 melanoma cells. In the FACS experiment, PC3 cells confirmed a relatively high $\alpha_v\beta_3$ expression (45% of cells showing fluorescent signal), consistent with values quoted in the cited literature, and a negligible expression (0.1%) of $\alpha_v\beta_3$ on Mat-Ly-Lu cells (FIG. 8).

Tumor Model

The experiment was performed on 10 Copenhagen rats (males) 11 weeks old, purchased from Harlan Laboratories Srl, S.Pietro al Natisone (UD), Italy. Rat prostate adenocarcinoma was induced in Copenhagen rats by orthotopic injection of the MatLylu tumor cells under isofluorane anesthesia. About 1 hour before tumor implantation, an analgesic (Rymadil) was administered subcutaneously (5 mg/kg) to rats. Then the lower abdomen was shaved and disinfected (Betadinen. A 12 mm incision of the abdominal wall along the linea Alba was performed 3 to 4 cm above the urinary orifice. The prostate was exposed after having pushed away the adipose tissue on each side of the animal. A cell suspension (30 µL) containing $0.5 \times 10^6$ tumor cells was injected with a 27G needle into the right ventral lobe of the prostate. The muscular and cutaneous plan was sewed up with sterile non-resorbable thread (3-0 black silk, Distrex S.p.a.). The wound was painted with disinfectant solution Betadine®. The analgesic was also administered at least once after surgery (about 24 h after). All procedures involving the animals have been conducted according to national and international laws and policies for the Care and Use of Laboratory Animals (EEC Council Directive 86/609CEE; L.D. 116/92 and EEC Council Directive 2010/63/EU; L.D. 26/2014. Authorization n.149/2006-A issued Oct. 27, 2006 by the Italian Ministry of Health).

Fluorescence-Guided Surgery Experiment

The tumor removal was performed using a dedicated surgical microscope (Axio Zoom v16, Carl Zeiss Beteiligungs GmbH, Jena, Germany). The microscope was equipped with a PLANAPO Z 0.5×/0.125 FWD 114 MM objective. During surgery an area of about $2.5 \times 2.5$ cm$^2$ was visualized. The surgical field was white-light illuminated by a cold light source (CL 9000 LED CAN (D)) when the fluorescence signal was not required, and by filtered light during the tumor removal (Illuminator: HXP 200C (D), filter set: 32 Cy 5.5 shift free (E)).

The day before surgery, corresponding to 3-4 days after tumor implantation, animals were administered with a dose of DA364 test agent ranging from 5 to 20 nmol/rat. Twenty-four hours after probes injection, animals were anaesthetized with isofluorane gas 0.5% ($O_2$ 99.5%), secured on the surgical table in the supine position and prostate tumor will be exposed.

Figure 3:
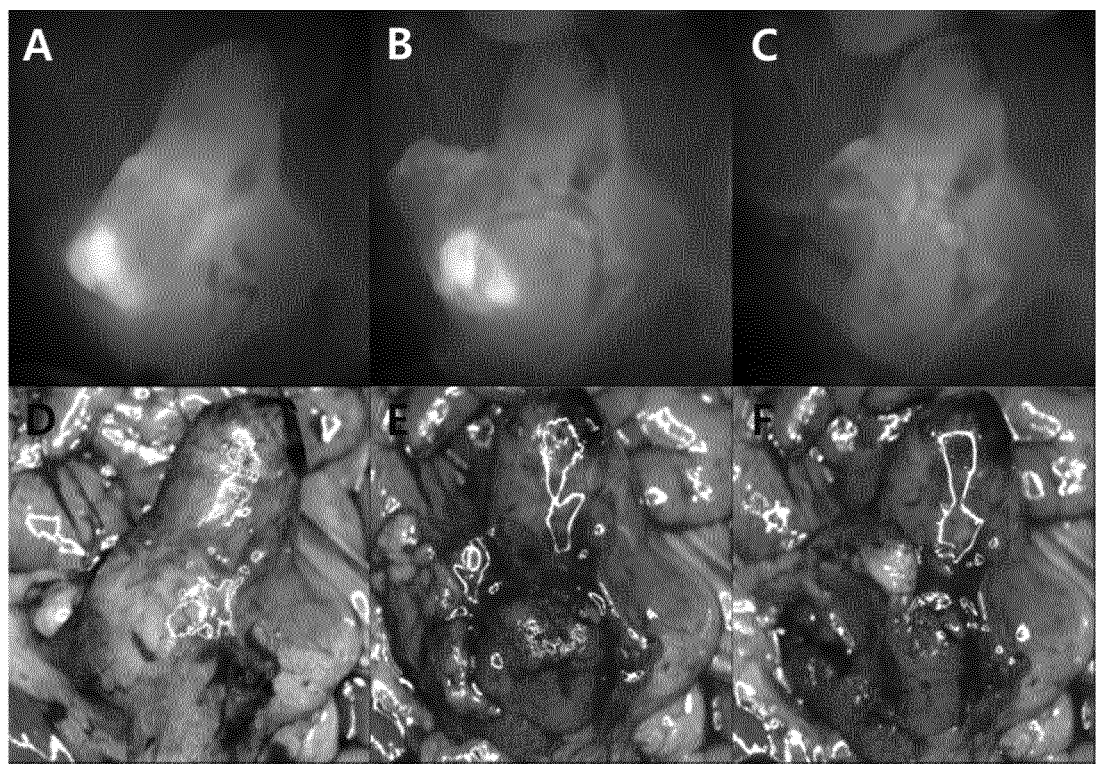
FIG. 3 shows fluorescent images (Panels A, B and C) acquired during the guided surgical procedure using DA364 and the corresponding images acquired under white light (Panels D, E and F). In particular: Panels A and D show intact prostate, in Panels B and E the prostate where the capsule of the right ventral lobe was removed, and Panels C and F show the surgical field at the end of the procedure.
Figure 4:
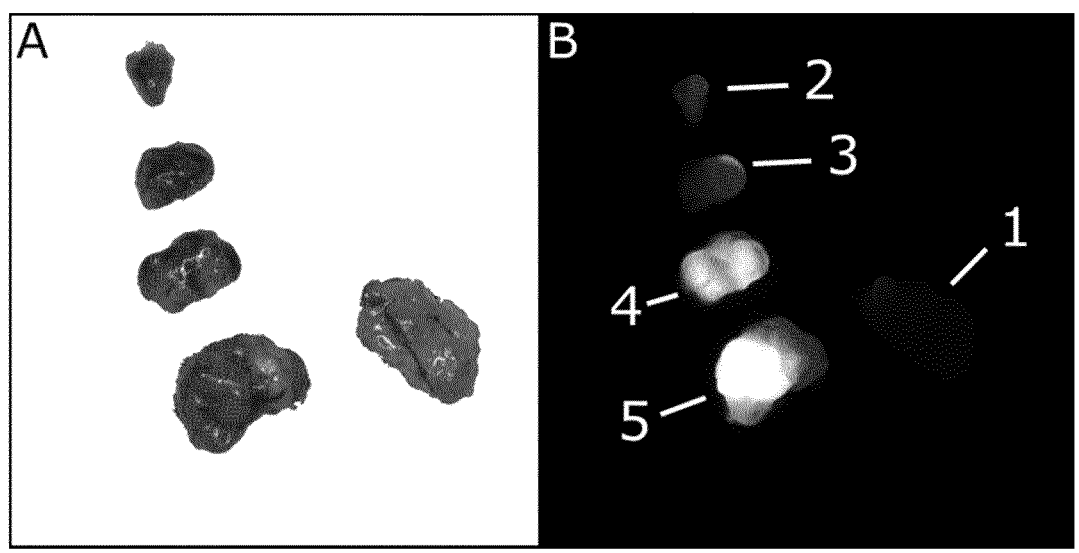
FIG. 4 shows excised tissue samples. In Panel A the tissue samples are imaged under white light and Panel B show the corresponding NIR fluorescent images.

After the removal of the prostatic capsule, the prostatic tumor was exposed to filtered light and fluorescence images were acquired to outline the primary tumor mass and the margins of the pathology (see FIG. 3, Panels A and D). The removal of the tumor mass was then carried out iteratively, by using fluorescence to guide the excision until absence of the fluorescent signal in the area surrounding tumor region (see FIG. 3, Panels B,E and C,F). Most of the fluorescent signal was confined in implantation area, i.e. the prostate right ventral lobe. Tissue samples excised from the area surrounding the fluorescence signal and left ventral, dorsal and anterior prostate lobes were collected and ex vivo fluorescence images were acquired to investigate the histological pattern underlying the accumulation of the fluorophore (FIG. 4). Of note, in this experimental test the samples of tissue were excised strictly following the tumor margins identified by high intensity of the fluorescence signal, although for a safer surgical strategy, a larger excision volume including at least a minimum non-fluorescent, negative, margin is recommended. All the collected tissue samples were finally processed for the following histological analysis. At the end of the experiments animals were sacrificed by overdose of anesthesia.

Histological Analysis

Excised samples were directly embedded in Killik compound (Cryostat embedding medium) and immediately frozen in isopentane cooled down in liquid nitrogen.

The excised tissue blocks were cut into groups of three consecutive 10 µm thick slices for parallel labelling. Each tissue sample was then treated with the standard procedure for histo-pathological analysis. In particular, a histological staining of collected samples was performed with Hematoxylin and Eosin in order to detect and characterize the anatomical tumor margins in excised samples and to verify the presence of optional tumor cells in surrounding healthy prostate tissue, in order to assess and confirm the radical excision of the tumor with surgery.

The detection of the fluorescent agent DA364 distribution in excised tissue samples was operated on tissue slides, after thawing at room temperature (RT) and washing in PBS to remove Killik. Cell nuclei were stained with 4',6-diamidino-2-phenylindole (DAPI, cod.BML-AP402, Enzo Life Sciences) (5 µg/mL in PBS, 5 min). The plasma membrane was stained with 2 µg/mL of FITC-conjugated Wheat Germ Agglutinin (WGA) (cod.W11261 Life Technologies), in order to identify the internalized fraction of DA364. To this extent, tissues were visualized both with the Aperio digital scanner ScanScope FL, to acquire the whole stained section, and Leica DM2500 fluorescence microscope, for additional details.

Internalization in Tumor Cells

Figure 7:
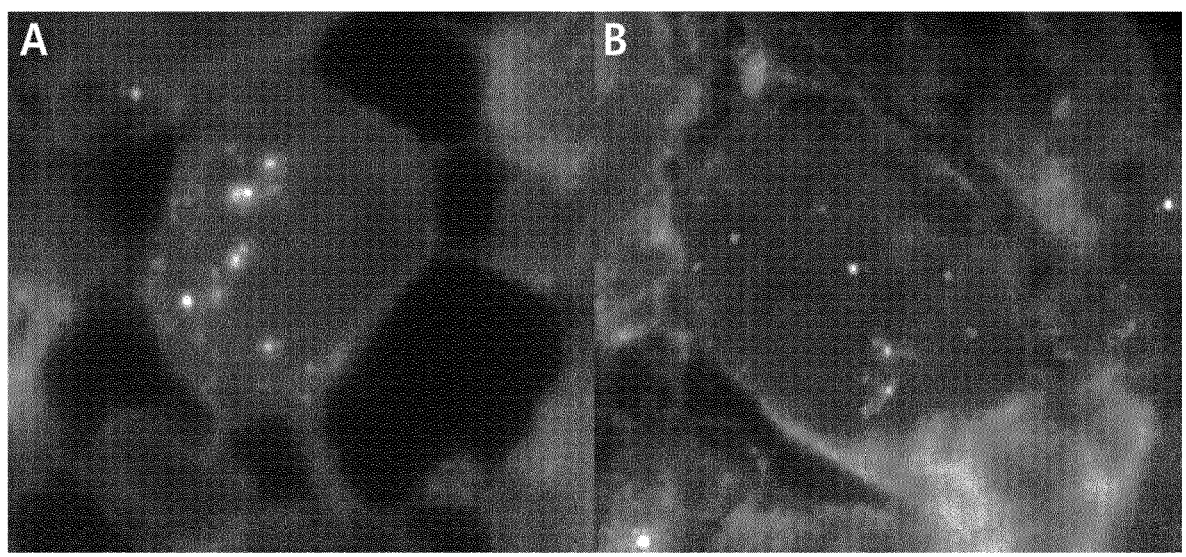
FIG. 7 Black and white images of Mat-Ly/Lu tumor cells in tissue slides obtained overlapping the signals from DA364 and the plasma membrane stain WGA.

The internalization of DA364 in tumor cells was then observed by fluorescence microscopy. In particular, black and white images of Mat-Ly/Lu tumor cells were obtained, for instance shown in FIG. 7, in which the fluorescent signal generated by DA364 is overimposed to the signal obtained from Mat-Ly/Lu tumor tissue slides stained with 2 µg/mL of FITC-conjugated Wheat Germ Agglutinin (WGA), a plasma membrane stain allowing to identify cells membranes and extracellular interstitial spaces.

Image Analysis

The ex vivo fluorescence images acquired just after surgery (FIG. 4) were used to visually classify the excised tissue samples in two fluorescence classes: FLUORESCENT and NON FLUORESCENT. The classification between the two fluorescence classes was based only on the fluorescent signal without considering the anatomic origin of the tissue sample. Tissue samples were assigned to the FLUORESCENT class when they included at least a region characterized by intense and bright fluorescent emission (see, for example, samples 3, 4 and 5 of FIG. 4). All remaining tissue samples, i.e. samples displaying no fluorescence (such as sample 1 of FIG. 4) or a fluorescence consistent with the autofluorescence observed in a healthy tissue far from the tumor area (such as sample 2 of FIG. 4) were classified in the NON FLUORESCENT class. For each image the fluorescent signal was mapped in pixels intensity using all the pixels intensity range. This classification procedure was intended to reproduce the fluorescence-based visual selection of 'Healthy' (NON FLUORESCENT) and 'Pathological' (FLUORESCENT) tissues that the surgeon is required to operate during the tumor removal.

Figure 5:
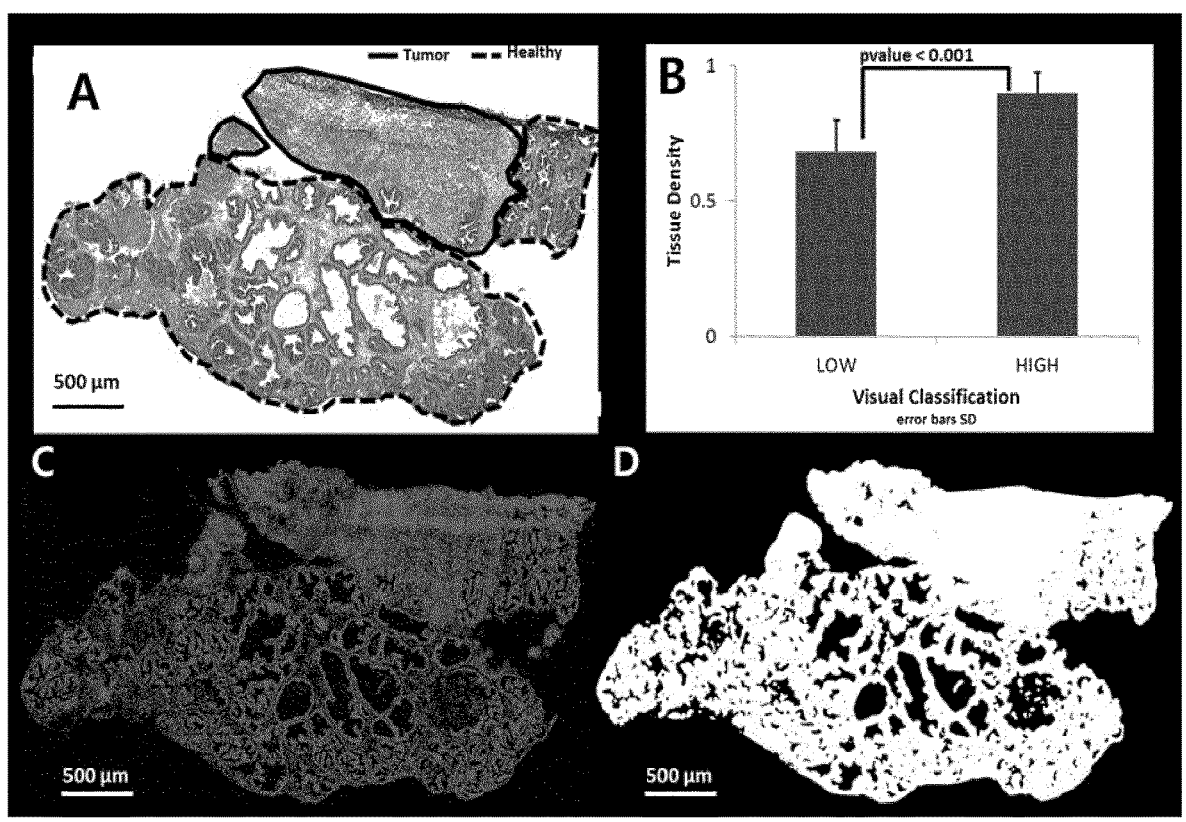
FIG. 5 shows the results of the histological validation of the florescence-based visual classification. In particular: Panel A shows an example of Hematoxylin/Eosin stained sections of prostate cancer showing healthy (LOWER density and LOWER FLUORESCENCE) and pathological (HIGH Density and higher FLUORESCENCE) areas; Paned C shows the fluorescence staining with DAPI, and the NON EMPTY AREA automatically detected in white is shown in panel D; Panel B reports the plot of the correspondence between histological and visual results for the parameter TISSUE DENSITY measured in sections from LOW and FLUORESCENT samples (pvalue <0.001, Mann Whitney U Test).

The results of the visual classification (of tissue samples collected during the guided surgery) were then validated histologically, by H&E staining of 2 histological sections from each tissue sample, allowing to identify sections containing a region of tumor, regardless of its dimension (FIG. 5 Panel A). Tissue samples containing tumor (namely tissues samples of which at least 1 of tested histological sections contained tumor cells) were then classified as POSITIVE, whereas tumor-free samples were classified as NEGATIVE. The histological and visual classifications were then compared using a contingency tables providing a measure the sensitivity of the visual classification enabled by the compound identified by the present invention and its reliability in identifying and separating tumor-free and tumor-containing tissues.

An additional analysis of collected tissue samples was also performed, based on the fluorescence of the nuclear stain 4',6-diamidino-2-phenylindole (DAPI). In general terms, this analysis relies on differences existing in the morphology of healthy and tumor tissues, where the normal prostatic morphology is disrupted by tumor invasion, that can be easily distinguished with an automatic threshold-based image analysis procedure (FIG. 5. Panels C,D). Healthy prostate tissue, in fact, is mainly constituted by glands and ducts immersed in a fibrous stroma; the empty regions of the tissue represent the wide lumen of prostatic glands, while epithelial glandular cells and stroma represent the parenchima of prostate. Tumor tissue, instead, is more typically constituted by homogeneously packed cells. This automatic procedure consisted in calculating the TISSUE DENSITY defined as the ratio of the sample area occupied by tissue (NON EMPTY AREA) versus the area of the section. Healthy tissues are characterized by a lower TISSUE DENSITY than pathological tissues.

Results

Histological Validation of the Surgical Efficacy.

The results of the histological and visual classifications were compared by using contingency tables. The results of the comparison, for instance included in the contingency Table E below, indicates that a significant correlation exists between the intensity of the detected fluorescence and the pathological state histologically verified in tested tissue samples. In particular, obtained results indicate that DA634 NIR fluorescent probe enabled a visual classification of tumor tissues with a sensitivity of 87% and a specificity of 83% (Table E).

FLUORESCENT samples were also characterized by a substantial disruption of the normal tissue morphology, by showing a statistically higher tissue density, essentially due to the absence of prostatic glands and ducts verified in pathologic tissues (Mann Whitney U test, p-value <0.05, FIG. 5, panel B).

TABLE E

Contingency table of the correspondences between visual and histological classification of tissue samples.

| Surgery | Histology | |
|---|---|---|
| | Positive | Negative |
| FLUORESCENT | 20 | 3 |
| NON FLUORESCENT | 3 | 15 |

Note: two of the three false negatives recorded in the test (NON-FLUORESCENT but POSITIVE) were tissue samples from the prostate capsule partially infiltrated by tumor cells, though displaying a low fluorescence at the surgical microscope, probably due to the elastic winding on itself caused by incision of the capsule, which made this particular prostatic region less visible and less properly imaged under fluorescent light. The remaining false negative was a very small piece of tissue removed from a big tumor that, when evaluated only by its fluorescence, showed low light intensity.

Example 8

Determination of $\alpha_v\beta_3$ Integrin Expression with Respect to Tumor Mass The expression of $\alpha_v\beta_3$ integrin has been measured by western blot, for three different types of tumors from animal models:

U-87 MG, a xenograft mouse model of human glioblastoma reported to have relative high expression of $\alpha_v\beta_3$ integrin MatLyLu, an orthotopic rat model of rat prostate cancer reported to have medium-low expression of $\alpha_v\beta_3$ integrin A431, a xenograft mouse model of human epidermoid carcinoma reported to have relatively low expression of $\alpha_v\beta_3$ integrin Methods Frozen tumor tissues were cut in small pieces using a scalpel and then pulverized, using a mortar and pestle, in presence of liquid nitrogen. The powder was weighted and then dissolved in an adequate volume of lysis buffer (Tris-HCl pH 8 50 mM, NaCl 150 mM, EDTA 1 mM, NaF 100 mM, glycerol 10%, MgCl2 1 mM, TritonX-100 1%, Protease Inhibitors), vortexed for 1 min, and put on ice for 45 min. Afterwards, the solution was sonicated 15 s and centrifuged 15 min at 4° C. at 14000 rpm.

The protein content of the supernatant was quantified with BCA method. Total extracts was loaded in a 10% polyacrylamide gel and electrophoresis was performed to separate the proteins by their molecular weight in denaturing conditions (20% SDS). Proteins within the gel were then transferred onto a nitrocellulose membrane and subsequently blotted with the antibody anti-β3 integrin. Specific signal was visualized as a single or multiple band by chemiluminescent detection method. The images of the labelled nitrocellulose were acquired by the ChemiDoc MP Imaging system and the area of the band relative to β3 expression level was quantified with the software Image Lab v.4.1

Results

The amount of integrin β3 was normalised by tumor mass (mg of tumor). The experiments were performed with at least two samples per tumor type. Results (mean value of integrin expression) are shown in Errore. L'origine riferimento non è stata trovata.

TABLE F

| Tumor type | Mean (ngβ$_3$/mg tumor) |
|---|---|
| U-87 MG | 16.28 |
| Matlylu | 6.8 |
| A431 | 2.39 |

Example 9

Determination of $\alpha_v\beta_3$ Integrin Expression with Respect to Total Amount of Protein in the Tumor Mass The expression of $\alpha_v\beta_3$ integrin has been measured by western blot, for the three different animal models previously detailed in Example 8 and for additional human tumors purchased as protein extracts.

The protein extracts from tumor models were obtained starting from tissues with the extraction method described before, while the human proteins extracts (as detailed below in table G) were purchased by OriGene

| Human Extract OriGene ID | Pathological Features |
|---|---|
| CP565523 | Malignant melanoma, metastatic IV |
| CP565782 | Adenocarcinoma of ovary, papillary serous IV (G2) |
| CP541289 | Adenocarcinoma of colon IV (G2) |

The data reported in table H below, further to confirming the respective reduced over-expression of $\alpha_v\beta_3$ integrin in Matlylu type tumor and A431 tumor, also show other human tumor with reduced expression of $\alpha_v\beta_3$ integrin which may benefit from the present invention.

TABLE H

| Type of Integrin β3 | ng β3/μg prot tot |
|---|---|
| Malignant Melanoma IV | 0.241149 |
| U-87 MG tumor (Hu in Ms) | 0.221000 |
| Matlylu tumor (Rt in Rt) | 0.104000 |
| A431 tumor (Hu in Ms) | 0.046500 |
| Ovarian adenocarcinoma IV (G2) | 0.027133 |
| Colorectal adenocarcinoma IV | 0.020731 |

Example 10

In Vivo Visualization of Tumors with Reduced Expression of $\alpha_v\beta_3$ Integrin (A431)

This example shows the uptake of DA364 in the A431 and U87-MG mouse models of human tumors, characterized respectively by low and high $\alpha_v\beta_3$ over-expression.

Tumor Model

A431 cells were collected and washed two times with PBS. Five million cells were resuspended in 0.1 mL of DMEM high glucose medium and subcutaneously injected in the right flank of all mice. Eleven days after A431 inoculation, U-87MG cells were collected and washed two times with PBS. Two million cells were resuspended in 0.1 mL of EMEM medium and subcutaneously injected in the left flank of same animals previously injected with A431 cells.

Tumors development was followed after inoculation by palpation and calliper measurement once a week. Tumor volume has been calculated according to the formula: $(L \times W^2)/2$, where L and W are the maximum length and width of the tumor. Animals were sacrificed by overdose of anaesthesia at the end of the experimental phase or in case the sum of both tumors reaches a volume of about 2000 mm$^3$.

Fluorescent Imaging Experiments

Three weeks after A431 tumor implantation five mice were administered with 1 nmol of DA364 for a total administration volume of 0.2 mL (inj. rate 1 mL/min). In vivo OI acquisitions have been carried out 5 min, 15 min, 30 min, 1 h, 2 h, 3 h, 4 h, 6 h, 24 h and 48 hours after intravenous administration of the fluorescent probe using the IVIS Spectrum optical imaging system (Perkin Elmer). During OI experiments animals were kept under 3-4% Sevofluorane gas anaesthesia (O$_2$ 97.0-96.0%). During anaesthesia animals body temperature has been stabilized at about 37° C. using a heated bed.

Following in vivo OI experiments, 48 hours after probes injection, animals were sacrificed. Tumors, liver, kidneys, heart and spleen were excised for ex vivo fluorescent signal measure on the whole excised tumor or organ.

Results

Fluorescence intensity from U-87 MG and A431 tumors was measured in vivo together with the signal coming from the normal healthy tissues (background).

Figure 9:
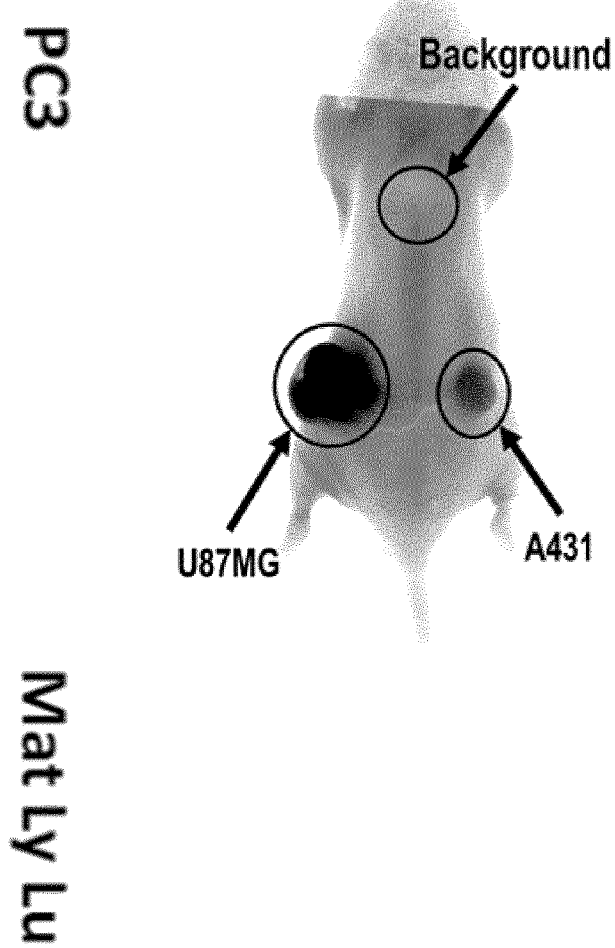
FIG. 9 illustrates the fluorescence imaging of U-87MG and the A431 tumros in a mouse.

In the time-window from 3 hours to 24 hours after injection, U-87 MG and A431 tumors showed stable signal ratio, with respect to the background. FIG. 9 illustrates the fluorescence imaging of a mice, showing that DA364 allows a clear visualization of the low-integrin expressing tumor A431 under skin.

The fluorescent signal (expressed as Radiant Efficiency (RE): $p/s/(\mu W/cm^2)$, where p is the photon count), was then measured on the excised ex vivo samples using the IVIS Spectrum optical imaging system (Perkin Elmer).

As illustrated in the table I below, the fluorescence signal of DA364 in U-87MG tumor was about twice the intensity of the signal measured in the A431 tumor. The fluorescence intensity measured in A431 tumors was however comparable to that measured in liver and kidney (excretion organs where DA364 accumulates)) while it was about 10 times higher with respect to the signal measured in heart and spleen (representative of heathy tissues, background).

TABLE I

| Tumor/Organ | Fluorescence Signal |
|---|---|
| U87-MG | 6.78E+08 |
| A431 | 3.47E+08 |
| liver | 4.04E+08 |
| kidney | 3.55E+08 |
| heart | 4.61E+07 |
| spleen | 5.79E+07 |

These results show that DA364 is a suitable imaging agent for tumors having reduced integrin expression, particularly for the intraoperative visualization thereof.

The invention claimed is:
1. A method of using a contrast agent of formula

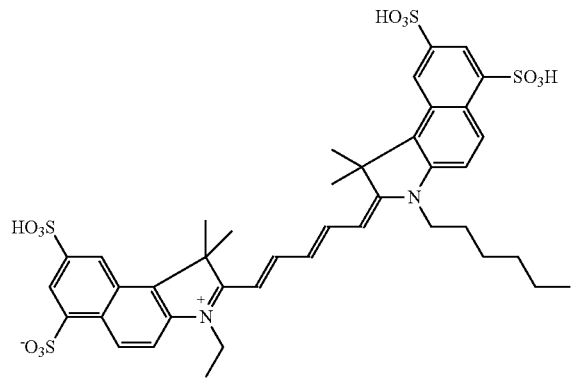

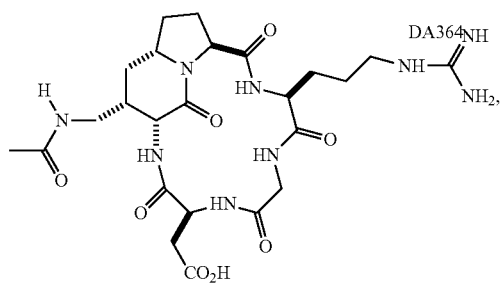

comprising administering an effective amount of the contrast agent in a patient, wherein the contrast agent is used as a fluorescent probe for a detection and demarcation of a tumor margin of a tumor in a surgery of the patient, and wherein the tumor shows a reduced or variable over-expression of $\alpha_v\beta_3$ integrin receptors, said expression being 0.15 ng of $\alpha_v\beta_3$ integrin/μg proteins or less.

2. The method according to claim 1, wherein the contrast agent is used for a real-time identification of a surgical border of a pathologic area under the surgery.

3. The method according to claim 1, wherein the detection and demarcation of the tumor margin is carried out under a fluorescent light that is capable of exciting the contrast agent.

4. The method according to claim 3, wherein the fluorescent light has a wavelength of from 630 to 690 nm.

5. The method according to claim 1, wherein the detection and demarcation comprises:
   illuminating, with a fluorescent light capable of exciting the contrast agent, a region comprising the tumor in the patient administered with the contrast agent; and
   identifying the tumor margin of the tumor under the fluorescent light.

6. The method according to claim 5, wherein the effective amount of the contrast agent is from 0.05 to 20 mg.

7. The method according to claim 6, wherein the patient is administered with the contrast agent within 48 hours before the surgery.

8. The method according to claim 1, wherein the tumor is selected from the group consisting of melanoma, glioma, glioblastoma, neuroblastoma, sarcoma, ovarian cancer, breast cancer, lung cancer, liver cancer, colon cancer, head-neck cancer, and prostate cancer.

9. The method according to claim 8, wherein the tumor is a prostate cancer.

10. The method according to claim 1, said expression being from 0.005 to 0.15 ng of $\alpha_v\beta_3$ integrin/μg proteins.

11. A method of using a pharmaceutical diagnostic composition comprising a contrast agent of formula

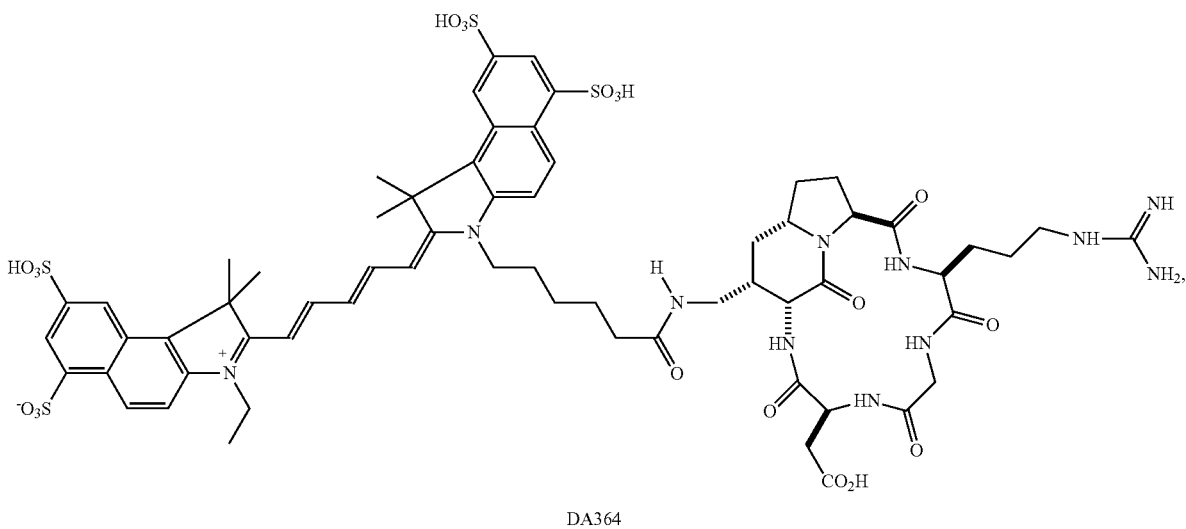

DA364 comprising administering the pharmaceutical diagnostic composition in a patient, wherein the pharmaceutical diagnostic composition is used in an intraoperative or a pre-operative optical imaging to provide a real-time detection and demarcation of a tumor margin of a tumor, and wherein the tumor shows a reduced or variable over-expression of $\alpha_v\beta_3$ integrin receptors, said expression being 0.15 ng of $\alpha_v\beta_3$ integrin/μg proteins or less.

12. The method according to claim 11, wherein the intraoperative or the pre-operative optical imaging is carried out in a surgery of a tumor of a patient to provide the real-time detection and demarcation of the tumor margin of the tumor undergoing a curative resection.

13. The method according to claim 11, said expression being from 0.005 to 0.15 ng of $\alpha_v\beta_3$ integrin/μg proteins.

14. A method of using a contrast agent of formula

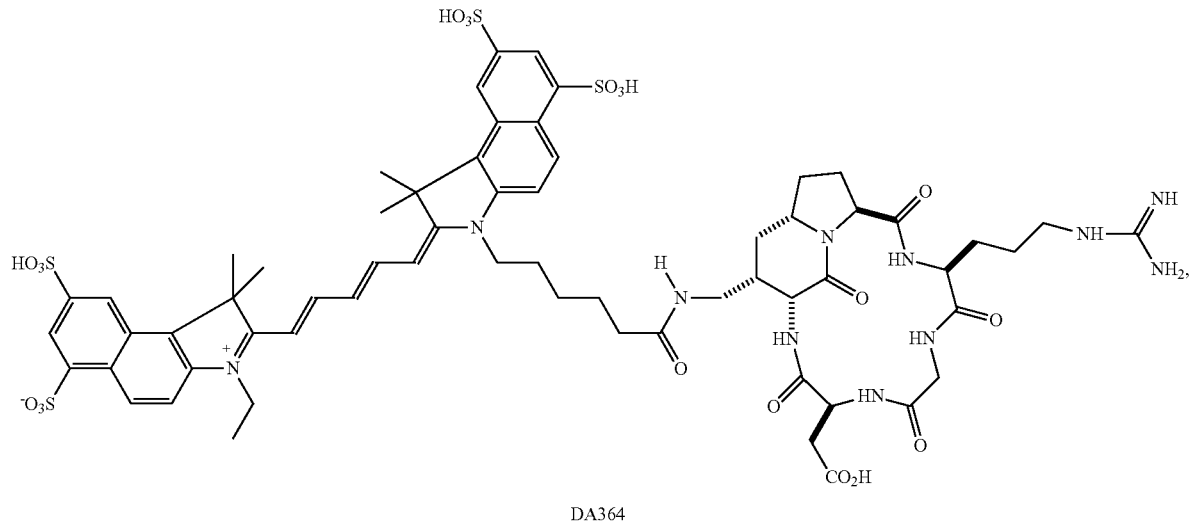

DA364 comprising:
illuminating a region in a patient with a fluorescent light capable of exciting the contrast agent, wherein the patient is pre-administered an effective amount of the contrast agent, and
detecting a tumor margin of a tumor under the fluorescent light, wherein the tumor shows a reduced or variable over-expression of $\alpha_v\beta_3$ integrin receptors, said expression being 0.15 ng of $\alpha_v\beta_3$ integrin/µg proteins or less.

15. The method according to claim 14, wherein the patient is pre-administered with from 0.05 to 20 mg of the contrast agent within one week before the step of detecting the tumor margin under the fluorescent light.

16. The method according to claim 14, wherein the step of detecting the tumor margin under the fluorescent light is performed in real-time, during a surgical inspection and a curative resection of the tumor.

17. The method according to claim 14 further comprising operating a curative resection of the tumor.

18. The method according to claim 14 comprising:
administering the effective amount of the contrast agent to the patient,
exposing the region of the patient to a surgeon's visual inspection,
illuminating the region of the patient with the fluorescent light capable of exciting the contrast agent,
generating an intraoperative image of the region of the patient,
detecting the tumor margin of the tumor under the fluorescent light,
operating a curative resection of the tumor by following the tumor margin, and
assessing the region under the fluorescent light and verifying the tumor including the tumor margin has been excised.

19. The method according to claim 18 further comprising repeating the step of operating the curative resection of the tumor by following the tumor margin.

20. The method according to claim 14, wherein the tumor is selected from the group consisting of melanoma, glioma, glioblastoma, neuroblastoma, sarcoma, ovarian cancer, breast cancer, lung cancer, liver cancer, colon cancer, head-neck cancer, and prostate cancer.

21. The method according to claim 14, said expression being from 0.005 to 0.15 ng of $\alpha_v\beta_3$ integrin/µg proteins.

* * * * *

UNITED STATES PATENT AND TRADEMARK OFFICE
CERTIFICATE OF CORRECTION

| | |
|---|---|
| PATENT NO. | : 10,682,427 B2 |
| APPLICATION NO. | : 15/535937 |
| DATED | : June 16, 2020 |
| INVENTOR(S) | : Maiocchi et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 227 days.

Signed and Sealed this
Tenth Day of January, 2023

Katherine Kelly Vidal
*Director of the United States Patent and Trademark Office*